United States Patent
Agopian et al.

(10) Patent No.: US 11,385,232 B2
(45) Date of Patent: Jul. 12, 2022

(54) PHENOTYPIC PROFILING OF HEPATOCELLULAR CARCINOMA CIRCULATING TUMOR CELLS FOR TREATMENT SELECTION

(71) Applicant: THE REGENTS OF THE UNIVERSITY OF CALIFORNIA, Oakland, CA (US)

(72) Inventors: Vatche Agopian, Los Angeles, CA (US); Hsian-Rong Tseng, Los Angeles, CA (US); Shuang Hou, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/641,955

(22) PCT Filed: Aug. 31, 2018

(86) PCT No.: PCT/US2018/049249
§ 371 (c)(1),
(2) Date: Feb. 25, 2020

(87) PCT Pub. No.: WO2019/046807
PCT Pub. Date: Mar. 7, 2019

(65) Prior Publication Data
US 2020/0182877 A1      Jun. 11, 2020

Related U.S. Application Data

(60) Provisional application No. 62/553,742, filed on Sep. 1, 2017.

(51) Int. Cl.
*G01N 33/574* (2006.01)
*C07K 16/28* (2006.01)
(Continued)

(52) U.S. Cl.
CPC ... *G01N 33/57438* (2013.01); *C07K 16/2851* (2013.01); *C07K 16/303* (2013.01);
(Continued)

(58) Field of Classification Search
CPC ....... G01N 33/57438; G01N 33/54306; G01N 33/54346; G01N 2800/085; C07K 16/2851; C07K 16/303
See application file for complete search history.

(56) References Cited

U.S. PATENT DOCUMENTS

2015/0316555 A1  11/2015  Fuchs et al.
2016/0009812 A1   1/2016  Satelli et al.
(Continued)

FOREIGN PATENT DOCUMENTS

CN       104807996 A      7/2015
WO    WO2014037552 A1     3/2014

OTHER PUBLICATIONS

Over Mu et al. Identification of biomarkers for hepatocellular carcinoma by semiquantitative immunocytochemistry. World J. Gastroenterol 20 (19): 5826-5838 (May 21, 2014).*
(Continued)

*Primary Examiner* — Gailene Gabel
(74) *Attorney, Agent, or Firm* — Karen S. Canady; canady + lortz LLP

(57) ABSTRACT

Methods and kits for detecting hepatocellular carcinoma recurrence or metastasis, and of measuring markers of hepatocellular carcinoma, including markers of hepatocellular carcinoma recurrence or metastasis, in a blood sample obtained from a subject by (a) isolating circulating tumor cells (CTCs) by contacting a blood sample obtained from the subject with a set of capture antibodies, wherein the capture antibodies specifically bind asialoglycoprotein receptor (ASGPR), Glypican-3, and epithelial cell adhesion molecule
(Continued)

(EpCAM); (b) contacting the isolated CTCs with an antibody that specifically binds vimentin; and (c) measuring the number of vimentin-positive CTC.

15 Claims, 11 Drawing Sheets

(51) Int. Cl.
    *C07K 16/30*     (2006.01)
    *G01N 33/543*     (2006.01)

(52) U.S. Cl.
    CPC . *G01N 33/54306* (2013.01); *G01N 33/54346* (2013.01); *G01N 2800/085* (2013.01)

(56) References Cited

U.S. PATENT DOCUMENTS

| | | | |
|---|---|---|---|
| 2016/0116477 A1 | 4/2016 | Hoffman et al. | |
| 2017/0151339 A1* | 6/2017 | White | A61K 9/5169 |

OTHER PUBLICATIONS

Ogle et al. Detection of Circulating Tumour Cells (CTCs) in Hepatocellular Cancer (HCC) Patients using the Imagestream. Journal of Hepatology 40 (1): Suppl. 1, S95 Abstract No. P87 (Apr. 2014).*

International Search Report for PCT/US2018/049249 (WO2019046807 Published Mar. 7, 2019).

Mu et al. "Identification of biomarkers for hepatocellular carcinoma by semiquantitative immunocytochemistry," World Journal of Gastroenterology, May 21, 2014 (May 21, 2014), vol. 20, No. 19, pp. 5826-5838.

Sun et al. "Circulating stem cell-like epithelial cell adhesion molecule-positive tumor cells indicate poor prognosis of hepatocellular carcinoma after curative resection," Hepatology, Nov. 23, 2012 (Nov. 23, 2012), vol. 57, Issue 4, pp. 1458-1468.

Wang et al. "Current strategies for preventing the recurrence of hepatocellular carcinoma after liver transplantation," Hepatobiliary & Pancreatic Diseases International, Apr. 30, 2015 (Apr. 30, 2015), vol. 14, No. 2, pp. 145-149.

Court et al. "Phenotype Profiling of Circulating Tumor Cells as a Prognostic Biomarker in Hepatocellular Carcinoma: Implications for Treatment Selection" 10th International Liver Cancer Association Annual Conference, Sep. 9, 2016, Abstract and Poster P-089.

Hu, Liang, et al., Association of Vimentin overexpression and hepatocellular carcinoma metastasis, Oncogene (2004) 23, 298-302.

Wu, Li-Jun, et al., Capturing circulating tumor cells of hepatocellular carcinoma, Cancer Letters 326 (2012) 17-22.

Extended European Search Report dated Apr. 22, 2021, received in related EP Application 18851615.7.

* cited by examiner

A.

B.

C.

PHENOTYPIC PROFILING OF HEPATOCELLULAR CARCINOMA CIRCULATING TUMOR CELLS FOR TREATMENT SELECTION

ACKNOWLEDGEMENT OF GOVERNMENT SUPPORT

This invention was made with Government support under CA198900, awarded by the National Institutes of Health. The Government has certain rights in the invention.

BACKGROUND OF THE INVENTION

Hepatocellular carcinoma (HCC) is an aggressive primary liver malignancy arising in the setting of end-stage liver disease, and is the 2nd leading cause of cancer mortality worldwide. Recurrence of hepatocellular carcinoma (HCC) following curative liver transplantation (LT) is a significant cause of patient mortality and loss of scarce donor allografts, and is not accurately predicted by current radiological staging criteria used to select candidates for LT.

There remains a need for a non-invasive diagnostic technology for the detection of underlying aggressive or occult metastatic disease to aid in the selection of HCC candidates for LT.

SUMMARY OF THE INVENTION

The assay reagents and methods described herein overcome problems relating to poor discrimination of markers for tumor biology and in current clinicopathologic staging systems, as well as addressing other needs. The disclosure herein provide methods of detecting hepatocellular carcinoma recurrence or metastasis, and of measuring markers of hepatocellular carcinoma, including markers of hepatocellular carcinoma recurrence or metastasis, in a blood sample obtained from a subject. The methods described herein accurately discriminate early-stage, liver transplant eligible patients from locally advanced, metastatic, liver transplant ineligible patients.

In one embodiment, the method comprises: (a) isolating circulating tumor cells (CTCs) by contacting a blood sample obtained from the subject with a set of capture antibodies, wherein the capture antibodies specifically bind asialoglycoprotein receptor (ASGPR), Glypican-3, and epithelial cell adhesion molecule (EpCAM). The method further comprises: (b) contacting the isolated CTCs with an antibody that specifically binds vimentin. In some embodiments, the method further comprises: (c) measuring the number of vimentin-positive CTC per 4 ml blood of the sample, wherein hepatocellular carcinoma recurrence or metastasis is detected if 2 or more vimentin-positive CTCs per 4 ml blood are present in the sample. In other embodiments, the method further comprises: (c) assigning a status score that reflects the measured amount of vimentin-positive isolated CTCs per volume of blood sample. In one embodiment, the vimentin-positive cells are cytokeratin-positive and CD45-negative.

In some embodiments, optionally, the method further comprises (d) referring the subject for surgical transplant. Typically, the subject is referred for transplant if the status score is less than 2 vimentin-positive CTC per 4 ml blood. In some embodiments, the subject is referred for treatment for hepatocellular carcinoma if the status score is greater than or equal to 2 vimentin-positive CTCs per 4 ml blood.

The methods described herein can optionally further comprise treating the subject for advanced or metastatic hepatocellular carcinoma.

The invention additionally provides a method of screening for advanced or metastatic hepatocellular carcinoma in a subject. In one embodiment, the method comprises performing the method steps recited above. Also provided is a method of identifying patients eligible for liver transplant. In one embodiment, the method comprises performing the method steps recited above.

The invention further provides a method of treating cirrhosis or other liver disease in a subject. In one embodiment, the method comprises: (a) isolating circulating tumor cells (CTCs) by contacting a blood sample obtained from the subject with a set of capture antibodies, wherein the capture antibodies specifically bind asialoglycoprotein receptor (ASGPR), Glypican-3, and epithelial cell adhesion molecule (EpCAM); (b) contacting the isolated CTCs with an antibody that specifically binds vimentin; (c) measuring the amount of vimentin-positive isolated CTCs per volume of blood sample; and (d) treating the subject with liver transplant if the status score is less than 2 vimentin-positive CTC per 4 ml blood, or treating the subject for hepatocellular carcinoma if the status score is greater than or equal to 2 vimentin-positive CTCs per 4 ml blood.

In the above methods, steps (a) and (b) can be performed separately or concomitantly. In some embodiments, the contacting of steps (a) and/or (b) are performed using a surface, such as a microarray or nanosurface, to which the antibodies are bound. The nanosurface can be prepared as a microfluidic, antibody based CTC enrichment assay. This assay serves to efficiently capture and characterize CTC phenotypes of prognostic importance in HCC. The modular NanoVelcro CTC platform has engrafted streptavidin on its nanosurface, allowing for any biotinylated cell-surface antibody to be employed for the capture of CTCs.

In some embodiments, the contacting of step (a) is performed with all of the capture antibodies bound to a single surface. In some embodiments, the capture antibodies are bound to the surface via biotin-streptavidin binding. In some embodiments, the contacting of step (a) is performed separately with each of the capture antibodies.

The methods described herein can be performed using, for example, immunoassay techniques, such as enzyme immunoassays, microarray assays, and nanosurface assays. Other assays can be employed, as will be understood to those skilled in the art. For use in the methods described herein, representative examples of the sample include, but are not limited to, blood, plasma or serum, and other bodily fluids. In a typical embodiment, the sample is blood or other bodily fluid containing circulating cells, such as PBMCs.

Also provided is a kit useful in carrying out the methods described herein. In one embodiment, the kit comprises: (a) a set of capture antibodies, wherein the capture antibodies specifically bind asialoglycoprotein receptor (ASGPR), Glypican-3, and epithelial cell adhesion molecule (EpCAM); and (b) an antibody that specifically binds vimentin. Optionally, the kit further comprises: (c) a surface to which the set of capture antibodies are bound.

Figure 2:
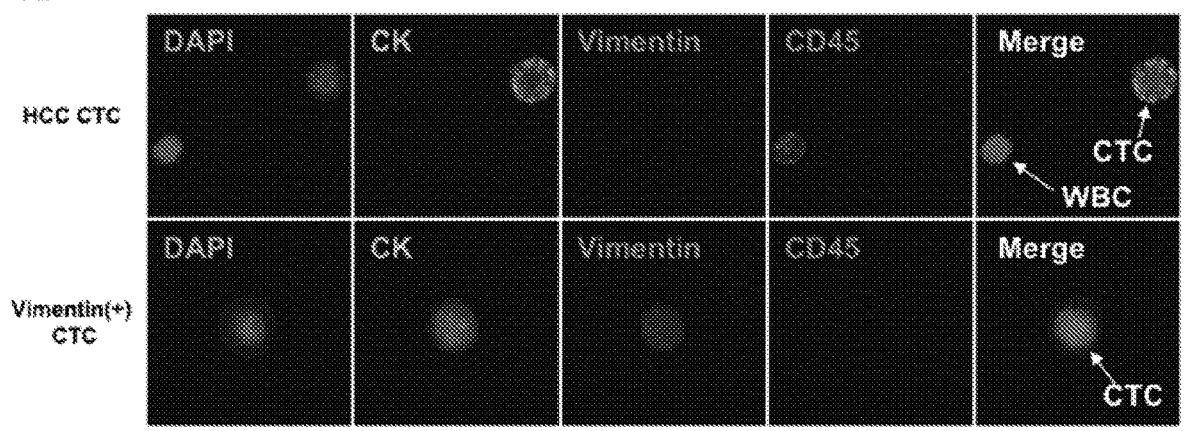
Figure 2:
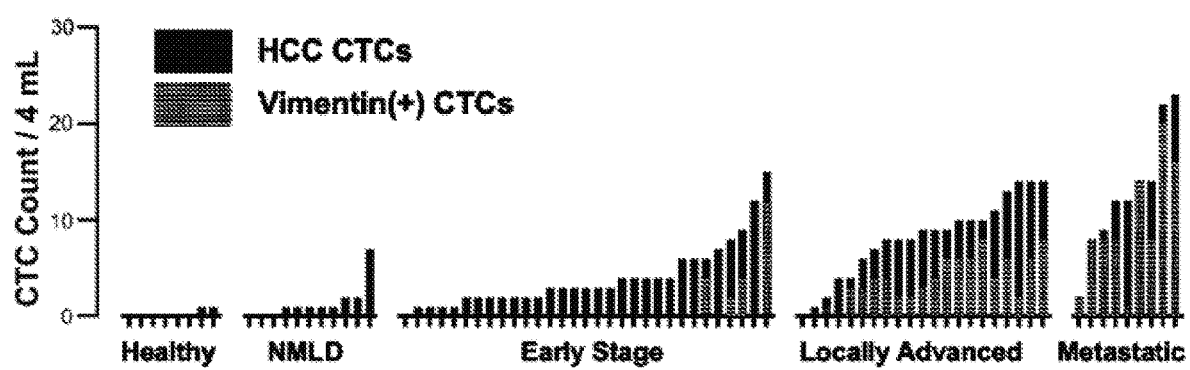

FIG. 2. (A) Schematic depicting CTC identification via a 4-color ICC approach in conjunction with high-resolution fluorescent microscopy. Representative images of a HCC-CTC and the subpopulation of vimentin(+) CTCs shown at 400× magnification. The WBC staining pattern can be seen in the cell in the lower left corner of the HCC-CTC image. (B) CTC counts for both HCC CTCs and vimentin(+) CTCs for all patients enrolled in the study (n=80). Patients are divided into groups based on staging criteria and sorted within groups based on total CTC count Healthy indicates controls without HCC or other identified liver disease.

Figure 3:
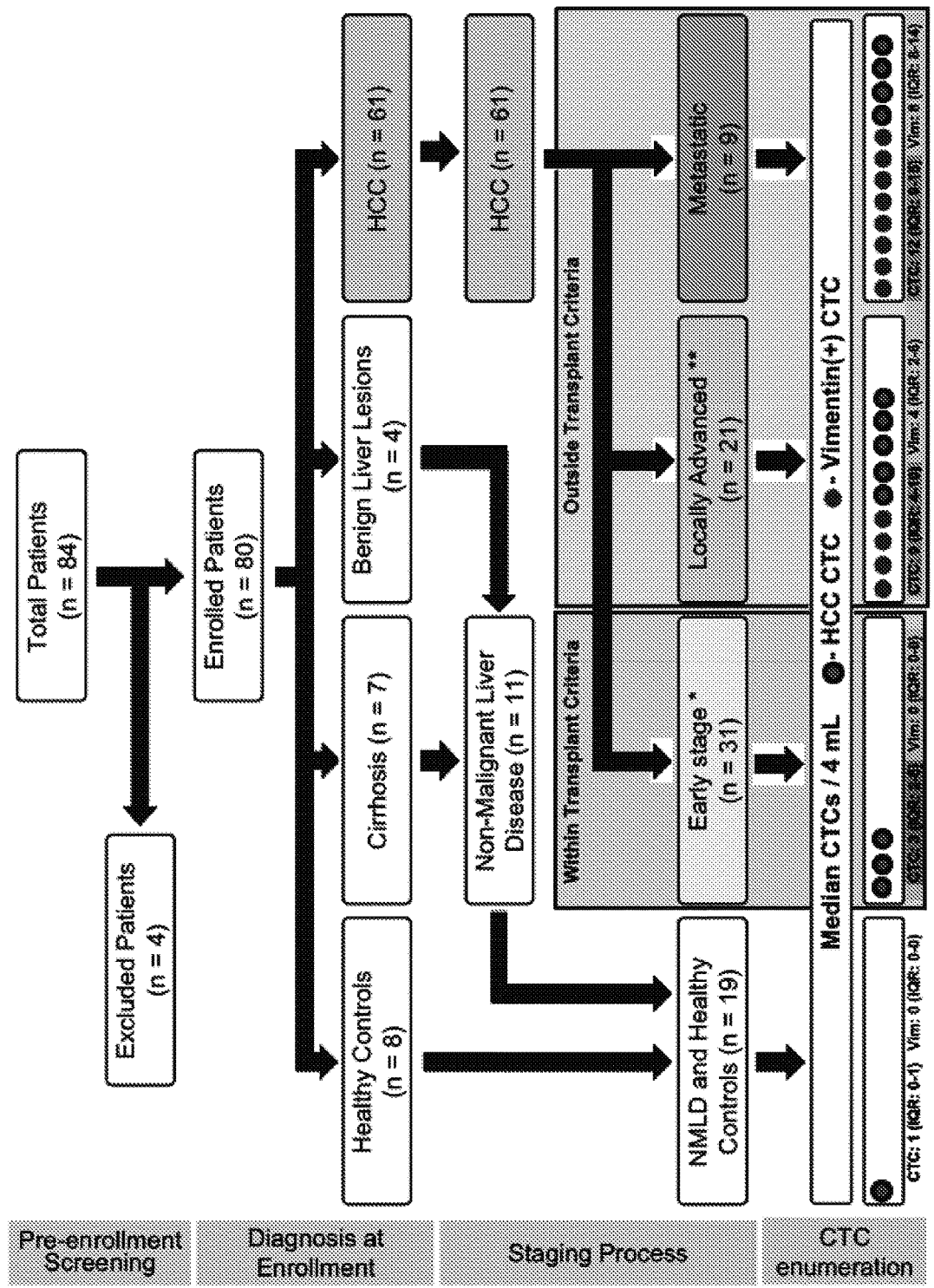

FIG. 3. Diagnosis and staging flowchart for patients enrolled in the study as well as associated CTC counts listed as median(IQR) for HCC-CTCs and Vimentin(+) CTCs. *Early Stage: patients with lesions within UCSF radiographic staging criteria; **Locally Advanced: patients with lesions larger than UCSF criteria but without evidence of metastatic disease.

Figure 4:
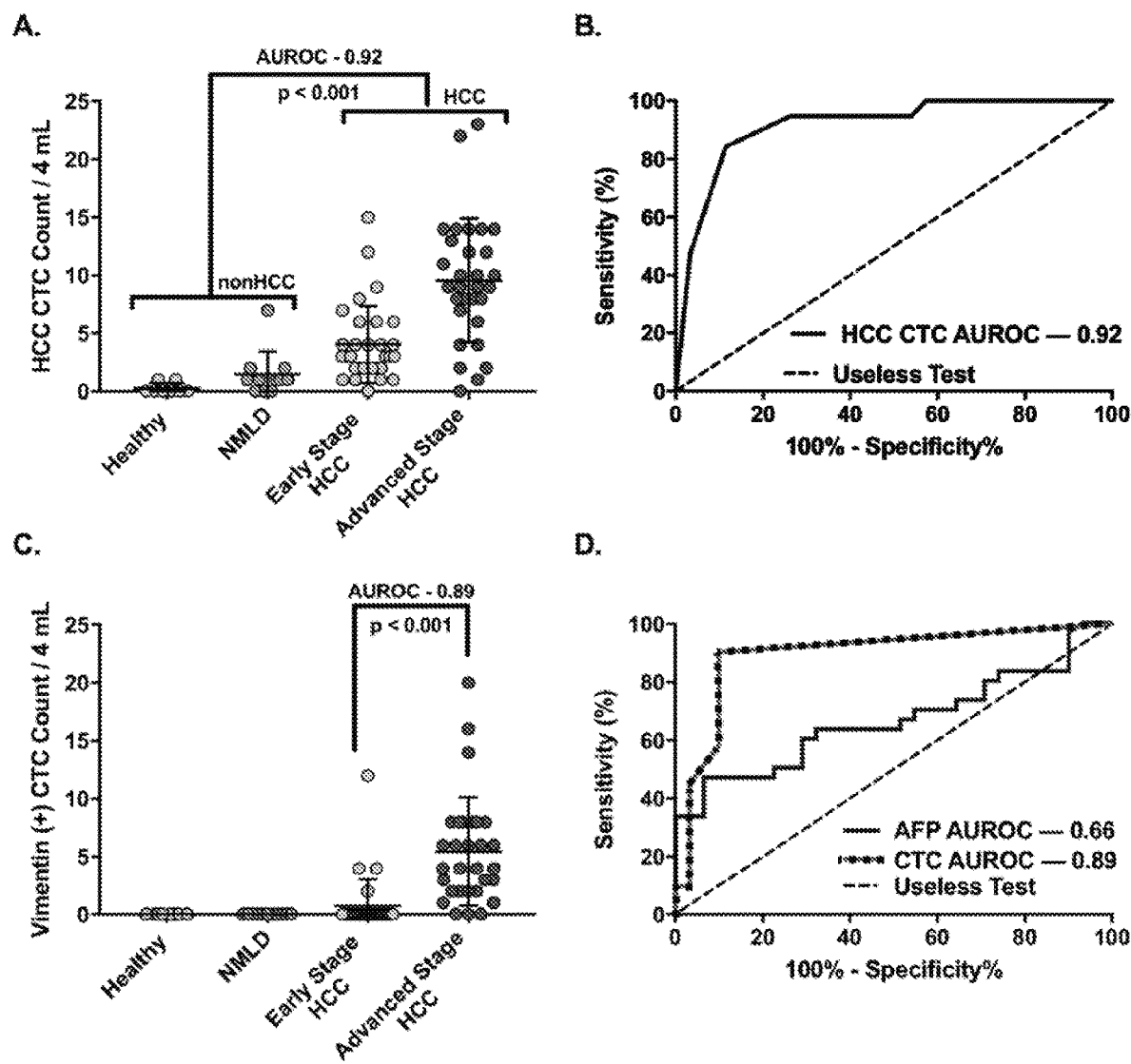

FIG. 4. (A) CTC enumeration in patients with local or advanced HCC versus NMLD or healthy controls. Advanced stage patients include patients with locally advanced disease and metastatic disease (B) ROC curve for illustration of HCC CTC performance in the discrimination of HCC from NMLD or healthy controls. At a cutoff of ≥2 CTCs/4-mL VB, HCC CTC AUROC=0.92 (95% CI: 0.86-0.99, p<0.001). (C) Vimentin(+) CTC enumeration in patients with early or advanced stage HCC versus nonHCC patients. (D) Comparison of the performance of vimentin(+) CTCs and AFP in discriminating early, potentially curable, HCC from advanced stage HCC. At a cutoff of ≥1 vimentin(+) CTCs/4-mL VB, AUROC=0.89 (95% CI: 0.74-0.95, p<0.001) versus AFP (cutoff: ≥1600 ng/mL), AUROC=0.66 (95% CI: 0.53-0.78, p=0.021).

Figure 5:
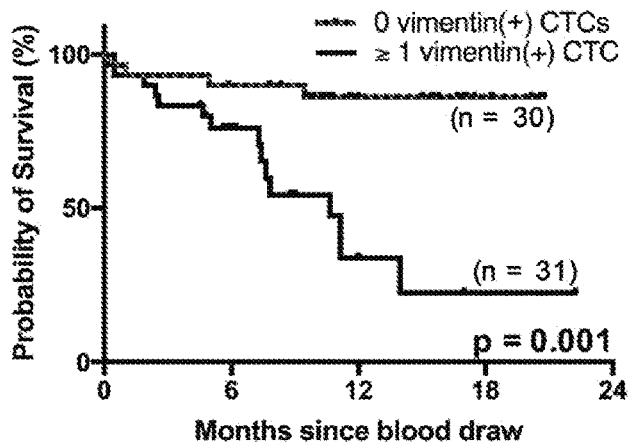
Figure 5:
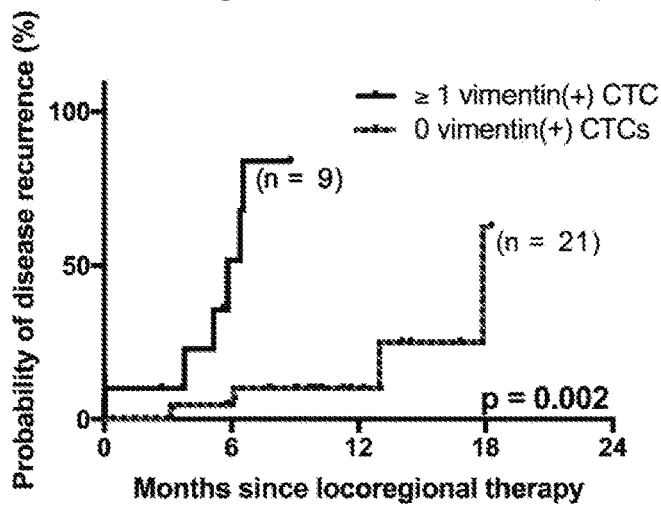
Figure 5:
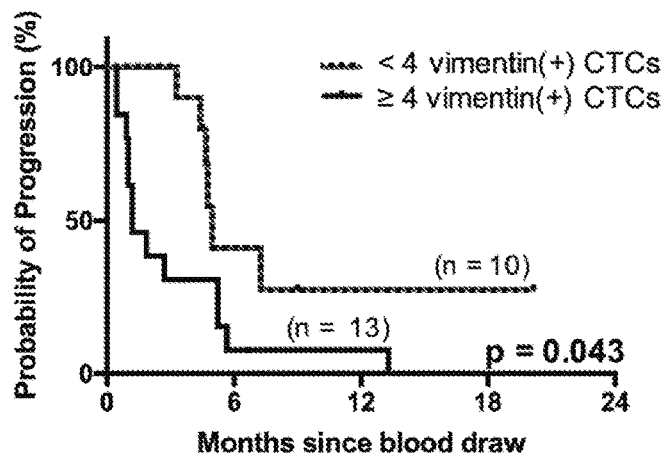

FIG. 5. (A) Overall survival at the optimized cutoff of ≥1 vimentin(+) CTC, all HCC patients. (B) Time to recurrence following potentially curative locoregional therapy at the optimized cutoff of ≥1 vimentin(+) CTC (n=30). (C) Progression-free survival at the optimized cutoff of ≥4 vimentin (+) CTCs, for patients with locally advanced or metastatic disease not amenable to potentially curative locoregional therapy (n=23).

Figure 6:
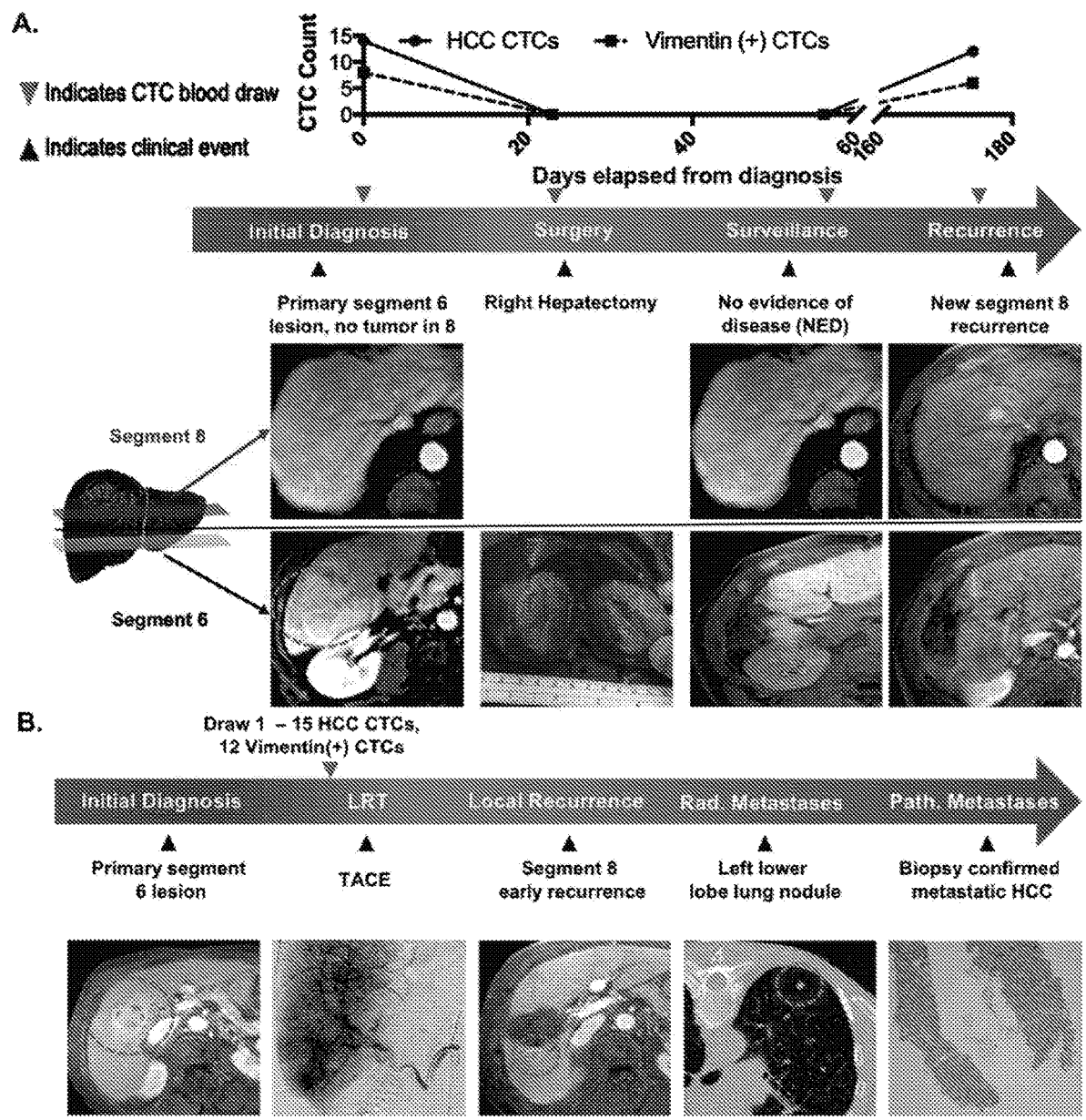

FIG. 6. Demonstration of the potential utility of the HCC-CTC Assay (A) Disease monitoring after surgical resection. Pre-surgical blood draw revealed 8 vimentin(+) CTCs (14 total HCC-CTCs), with subsequent CTC enumeration revealing no CTCs at 1 and 2 months following resection of a 5.8 cm HCC, consistent with surveillance MRI imaging revealing no evidence of recurrence. A 3rd post-resection blood draw revealed 6 vimentin(+) CTCs (12 total HCC-CTCs), presaging the subsequent MRI demonstration of a segment 8 HCC recurrence. (B) Vimentin(+) CTCs are highly predictive of earlier recurrence following potentially curative locoregional therapy, and appear to be a surrogate for patients who have tumors with aggressive underlying tumor biology. This patient had a solitary 4 cm right hepatic lobe HCC without evidence of metastases. Despite being radiographically staged as an early stage patient, she was found to have 12 vimentin(+) CTCs (15 HCC-CTCs total) prior to any treatment. Despite successful locoregional therapy with TACE, she soon developed multifocal HCC on her 1-month post-procedure scan with rapid development of metastatic lung nodules at 3-months post-procedure.

Figure 7:
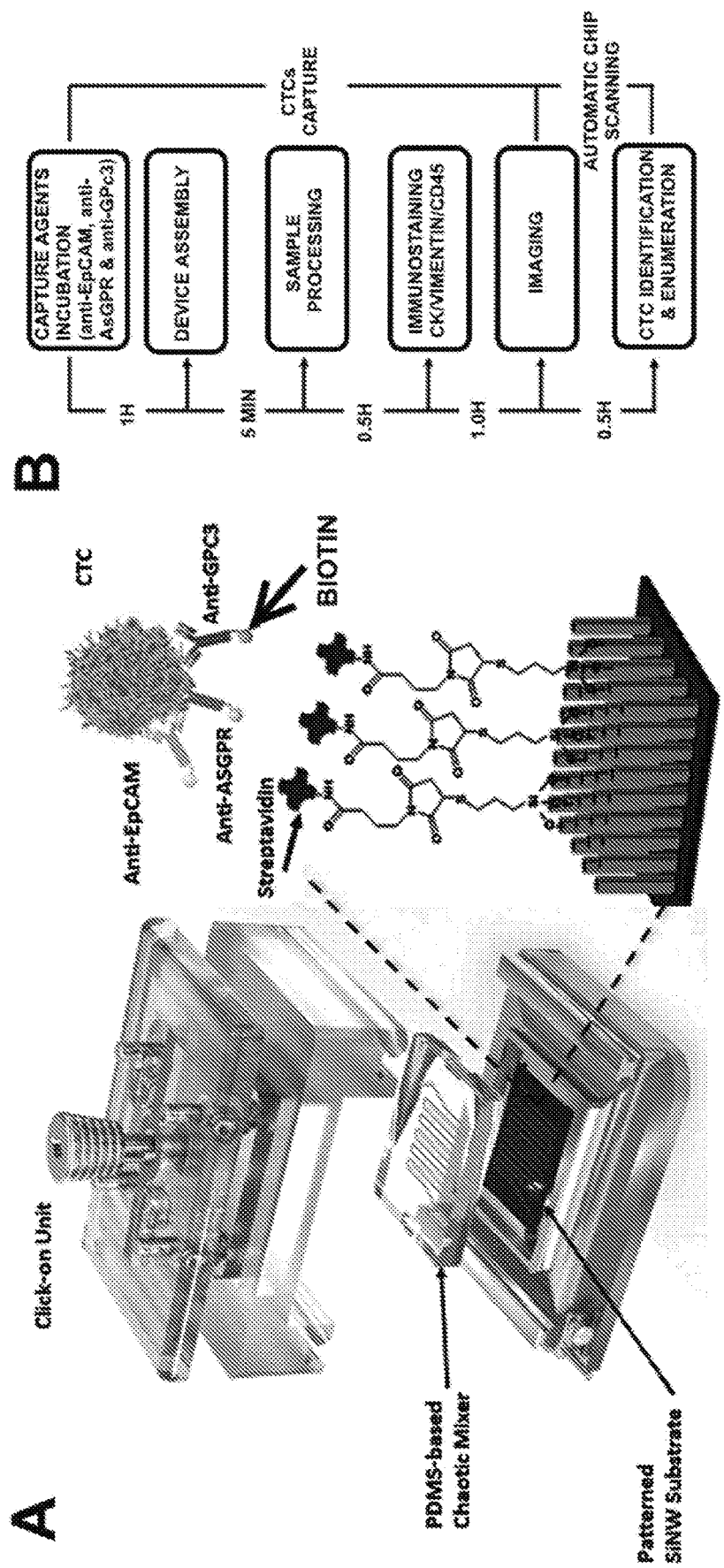

FIG. 7. (A) Schematic diagram of the components of the NanoVelcro CTC assay. The click-on unit compresses the PDMS-based chaotic mixer against the serpentine channels of the silicone nanowire chip to create a microfluidic channel which optimizes cellular interactions with the chip surface. In the cutout, the nanowire substrate can be seen functionalized with biotinylated capture antibodies adjoined using streptavidin binding. These capture antibodies are responsible for "capturing" the CTCs on the chip. (B) General workflow diagram for CTC capture, identification, and enumeration on SiNS NanoVelcro Chips. The schematic shows the individual components of SiNS NanoVelcro Chips, chip holding device, and elements/duration of the workflow for processing a typical blood sample. SiNW, silicone nanowire; PDMS, Polydimethylsiloxane; EpCAM, epithelial cell adhesion molecule; GPC-3, glypican-3; ASGPR, asialoglycoprotein receptor; CTC, circulating tumor cell.

Figure 8:
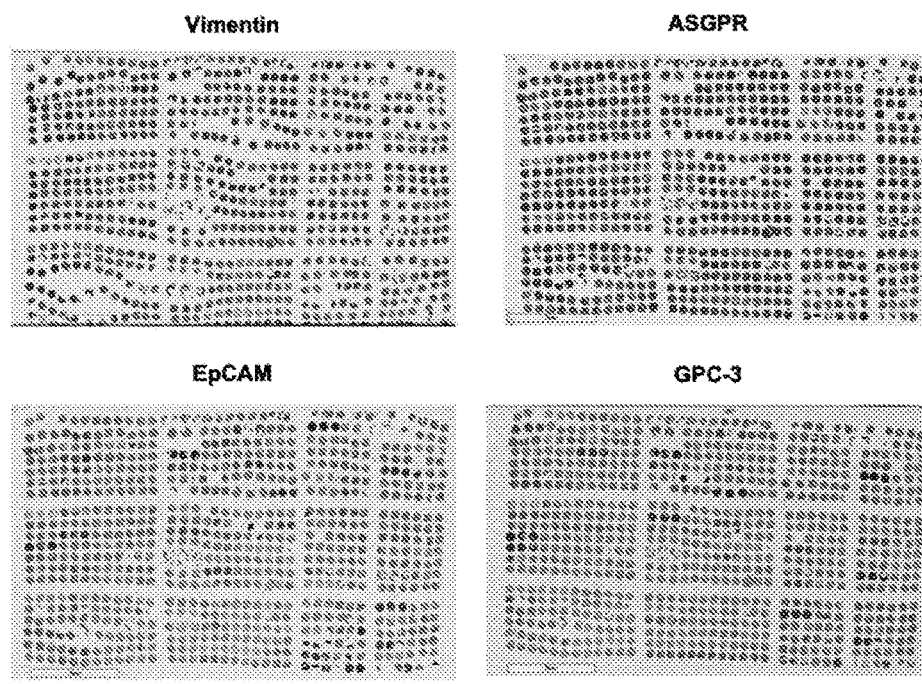

FIG. 8. Low power images of the entire tissue microarray stained with vimentin, ASGPR, EpCAM, and GPC-3. Many of the tumors appear positive for vimentin at low power due to staining of the sinusoidal endothelial lining and not the tumor itself. EpCAM, epithelial cell adhesion molecule; GPC-3, glypican-3; ASGPR, asialoglycoprotein receptor.

Figure 9:
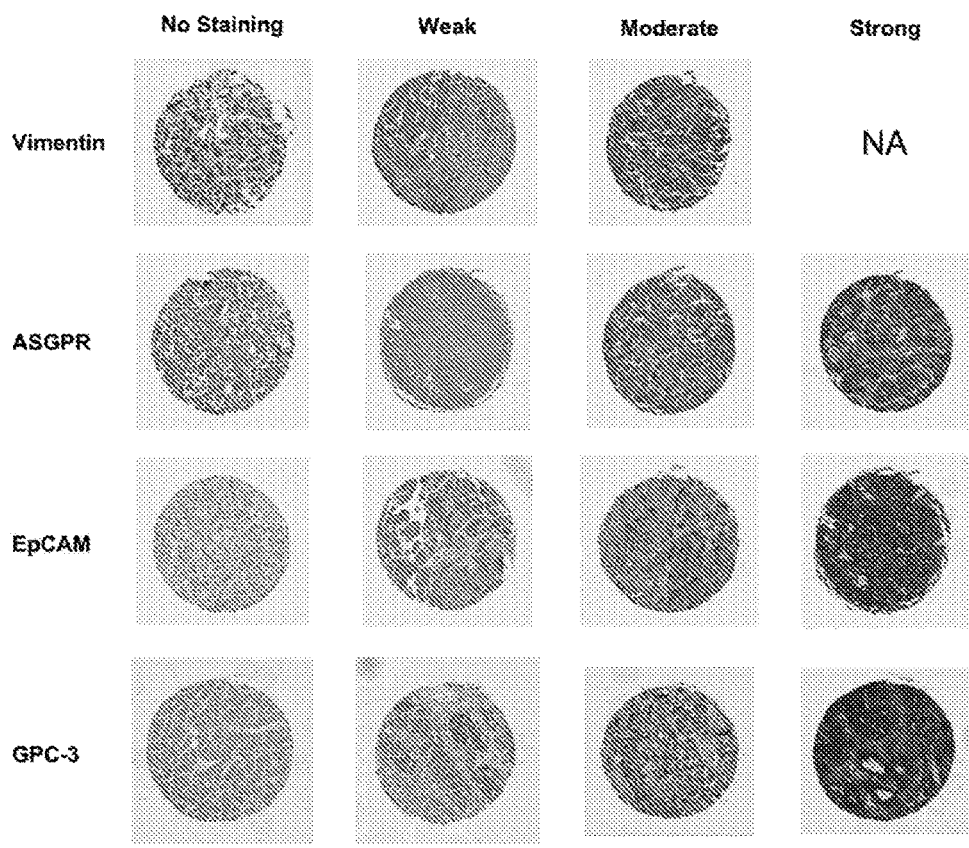

FIG. 9. Examples of staining intensity determinations for each of the antibodies used on the 114 patient TMA. None of the tumors stained strongly for vimentin. EpCAM, epithelial cell adhesion molecule; GPC-3, glypican-3; ASGPR, asialoglycoprotein receptor.

Figure 10:
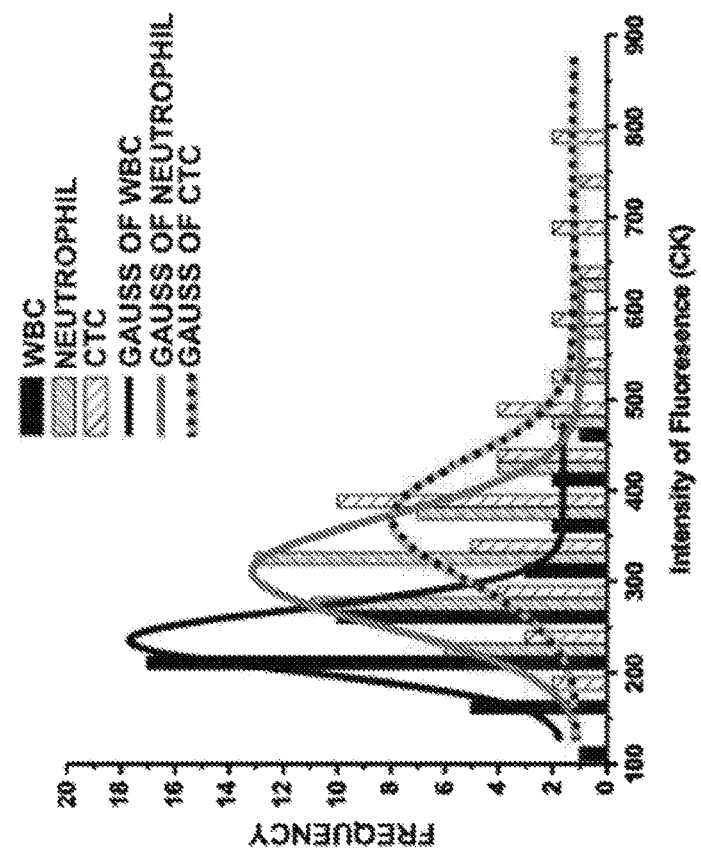
Figure 10:
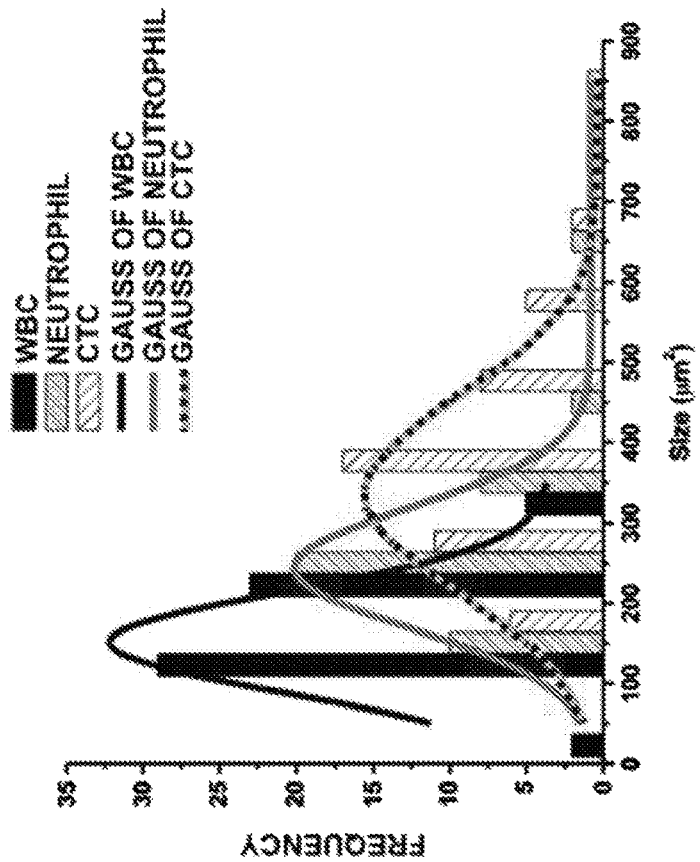

FIG. 10. Development of CTC size criteria cutoff. (A) Frequency of CTCs, WBCs, and neutrophils by cross-sectional size. (B) Frequency of CTCs, WBCs, and neutrophils by CK RFU.

Figure 11:
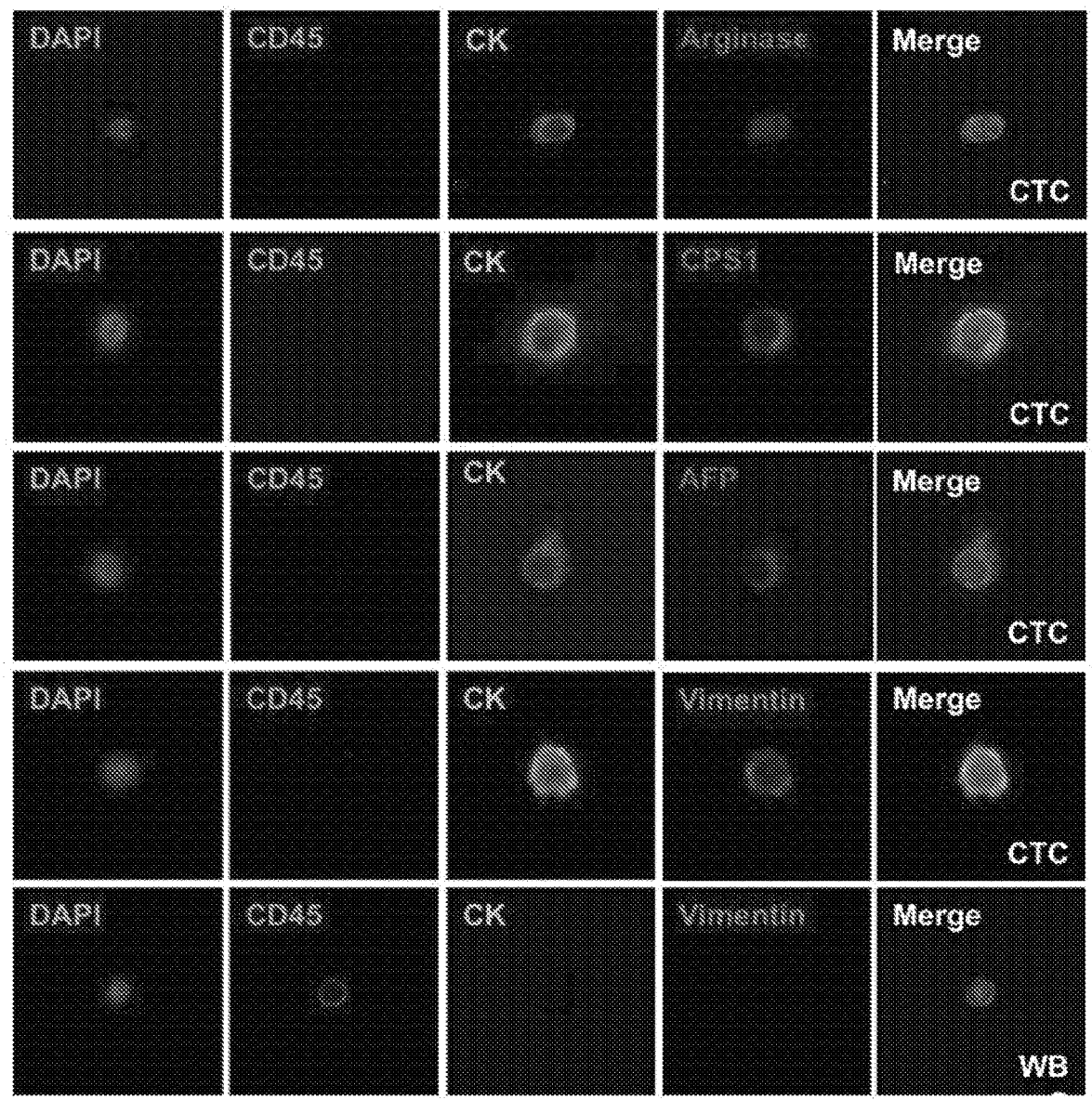

FIG. 11. Confirmation of hepatocyte origin of HCC CTCs. Hepatocyte specific markers considered for HCC CTC identification (Arginase, CPS1[Hep-Par1], AFP) were found to only stain CK+ CTCs, not CD45 WBCs. Additionally, EMT (vimentin) markers were tested. All cells were obtained from the blood of patients with HCC and identified on a 4-color immunocytochemical approach in conjunction with high-resolution fluorescent microscopy. DAPI, 4',6-diamidino-2-phenylindole; CK, cytokeratin; CPS1, carbamoyl-phosphate synthase 1; AFP, alpha-fetoprotein.

Figure 12:
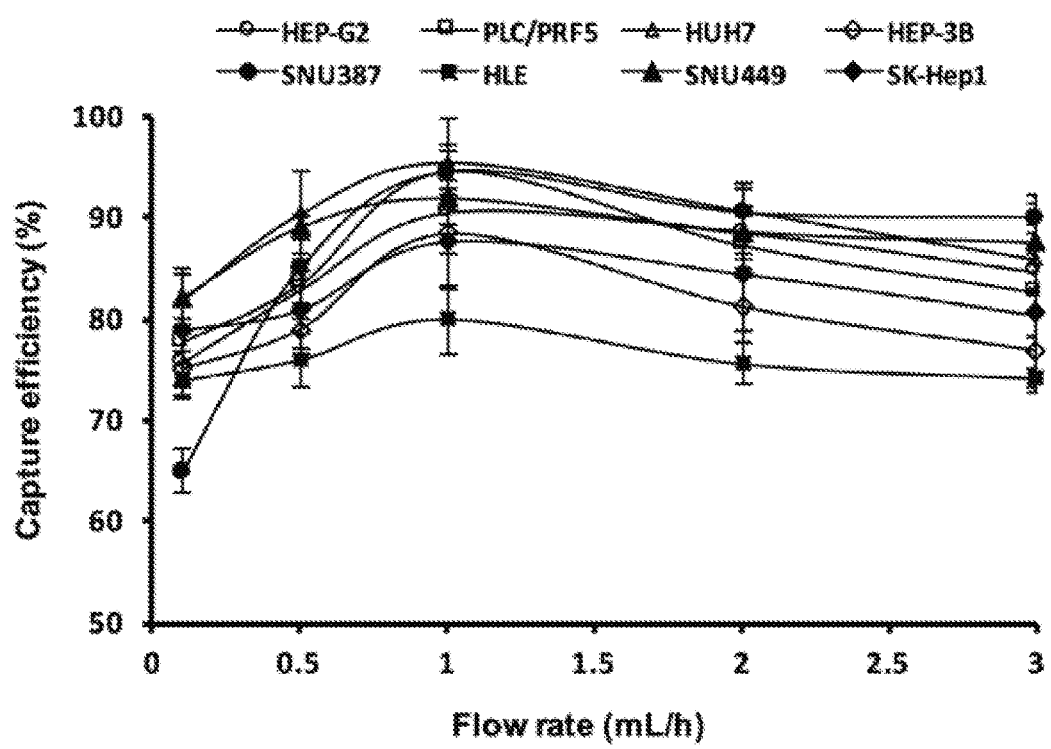
Figure 12:
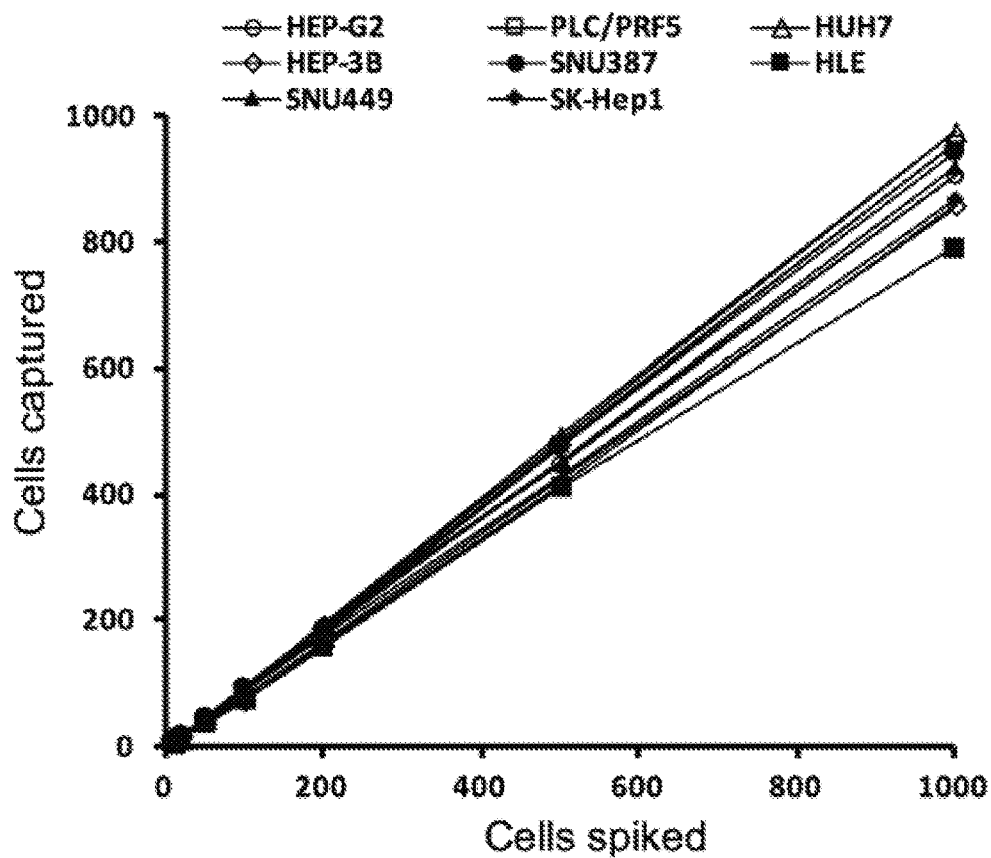

FIG. 12. Calibration of optimum microfluidic flow rate for CTC capture by NanoVelcro CTC assay. (A) Using 8 HCC cell lines, the cell capture efficiency of the NanoVelcro Chip was assessed at flow rates of 0.1, 0.5, 1, 2, and 3 mL/h. Data represents the mean ±SD (n=3). (B) Cell spiking experiments confirmed the capture efficiency of the assay for CTC concentrations as low as 10 cells in 2 mL of blood.

DETAILED DESCRIPTION OF THE INVENTION

The assay reagents, kits, and methods described herein overcome problems relating to poor discrimination of markers for tumor biology and in current clinicopathologic staging systems, as well as addressing other needs relating to the care and treatment of patients suffering from liver cancer and/or cirrhosis. The disclosure herein provides methods of detecting hepatocellular carcinoma recurrence or metastasis, and of measuring markers of hepatocellular carcinoma, including markers of hepatocellular carcinoma recurrence or metastasis, in a blood sample obtained from a subject. The methods described herein accurately discriminate early-stage, liver transplant eligible patients from locally advanced, metastatic, liver transplant ineligible patients.

Definitions

All scientific and technical terms used in this application have meanings commonly used in the art unless otherwise specified. As used in this application, the following words or phrases have the meanings specified.

As used herein, "bound" or "binding" refer to direct binding, e.g., antibody to antigen, as well as to indirect binding, such as may occur when a biotinylated antibody is bound to a streptavidin-coated surface via biotin-streptavidin binding.

A "microarray" is a linear or two-dimensional array of preferably discrete regions, each having a defined area, formed on the surface of a solid support.

The term "label" refers to a composition capable of producing a detectable signal indicative of the presence of the target in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "biological sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In a preferred embodiment, the sample is blood or other sample containing circulating cells, such as a fraction that includes peripheral blood mononuclear cells (PBMCs).

The term "antibody" is meant to be an immunoglobulin protein that is capable of specifically binding an antigen. Antibody as used herein is meant to include antibody fragments, e.g. F(ab')2, Fab', Fab, capable of binding the antigen or antigenic fragment of interest.

As used herein, "a" or "an" means at least one, unless clearly indicated otherwise.

As used herein, to "prevent" or "protect against" a condition or disease means to hinder, reduce or delay the onset or progression of the condition or disease.

As used herein, to "treat" a condition or disease means to ameliorate symptoms of the condition or disease.

Methods

Described herein are methods enabling the discrimination between different stages of hepatocellular carcinoma (HCC) and improved prognostication and treatment of patients. Circulating tumor cells are isolated and selected on the basis of vimentin positive status as an indicator of disease status and severity. In one embodiment, the method comprises: (a) isolating circulating tumor cells (CTCs) by contacting a blood sample obtained from the subject with a set of capture antibodies, wherein the capture antibodies specifically bind asialoglycoprotein receptor (ASGPR), Glypican-3, and epithelial cell adhesion molecule (EpCAM). The method further comprises: (b) contacting the isolated CTCs with an antibody that specifically binds vimentin. In some embodiments, the method further comprises: (c) measuring the number of vimentin-positive CTC per 4 ml blood of the sample, wherein hepatocellular carcinoma recurrence or metastasis is detected if 2 or more vimentin-positive CTCs per 4 ml blood are present in the sample. In other embodiments, the method further comprises: (c) assigning a status score that reflects the measured amount of vimentin-positive isolated CTCs per volume of blood sample. In one embodiment, the vimentin-positive cells are cytokeratin-positive and CD45-negative.

In some embodiments, optionally, the method further comprises (d) referring the subject for surgical transplant Typically, the subject is referred for transplant if the status score is less than 2 vimentin-positive CTC per 4 ml blood. In some embodiments, the subject is referred for treatment for hepatocellular carcinoma if the status score is greater than or equal to 2 vimentin-positive CTCs per 4 ml blood. The methods described herein can optionally further comprise treating the subject for advanced or metastatic hepatocellular carcinoma.

The invention additionally provides a method of screening for advanced or metastatic hepatocellular carcinoma in a subject. In one embodiment, the method comprises performing the method steps recited above. Also provided is a method of identifying patients eligible for liver transplant. In one embodiment, the method comprises performing the method steps recited above.

The invention further provides a method of treating cirrhosis or other liver disease in a subject. In one embodiment, the method comprises: (a) isolating circulating tumor cells (CTCs) by contacting a blood sample obtained from the subject with a set of capture antibodies, wherein the capture antibodies specifically bind asialoglycoprotein receptor (ASGPR), Glypican-3, and epithelial cell adhesion molecule (EpCAM); (b) contacting the isolated CTCs with an antibody that specifically binds vimentin; (c) measuring the amount of vimentin-positive isolated CTCs per volume of blood sample; and (d) treating the subject with liver transplant if the status score is less than 2 vimentin-positive CTC per 4 ml blood, or treating the subject for hepatocellular carcinoma if the status score is greater than or equal to 2 vimentin-positive CTCs per 4 ml blood.

In the above methods, steps (a) and (b) can be performed separately or concomitantly. In some embodiments, the contacting of steps (a) and/or (b) are performed using a surface, such as a microarray or nanosurface, to which the antibodies are bound. The nanosurface can be prepared as a microfluidic, antibody based CTC enrichment assay. This assay serves to efficiently capture and characterize CTC phenotypes of prognostic importance in HCC. The modular NanoVelcro CTC platform has engrafted streptavidin on its nanosurface, allowing for any biotinylated cell-surface antibody to be employed for the capture of CTCs. Those skilled in the art will appreciate other means by which antibodies can be used to capture CTCs, including other means of binding to a solid support and other means of detection.

In some embodiments, the contacting of step (a) is performed with all of the capture antibodies bound to a single surface. In some embodiments, the capture antibodies are bound to the surface via biotin-streptavidin binding, such as by use of biotinylated antibodies that bind to a streptavidin-coated surface. In some embodiments, the contacting of step (a) is performed separately with each of the capture antibodies. In some embodiments, a microarray is used to facilitate detection of specific binding. In some embodiments, specific binding is detected through the use of distinct markers or labels.

The methods described herein can be performed using, for example, immunoassay techniques, such as enzyme immunoassays, microarray assays, and nanosurface assays. Other assays can be employed, as will be understood to those skilled in the art. For use in the methods described herein, representative examples of the sample include, but are not limited to, blood, plasma or serum, and other bodily fluids.

Kits and Assay Standards

The invention provides kits comprising a set of reagents as described herein, such as antibodies that specifically bind one or more markers of the invention, and optionally, one or more suitable containers containing reagents of the invention. Reagents include molecules that specifically bind one or more markers of the invention, including antibodies that specifically bind asialoglycoprotein receptor (ASGPR), Glypican-3, and epithelial cell adhesion molecule (EpCAM), as well as antibodies that specifically bind vimentin. One example of a reagent is an antibody that is specific for the marker. Reagents can optionally include a detectable label. Labels can be fluorescent, luminescent, enzymatic, chromogenic, or radioactive. The kit can optionally include a buffer.

Kits of the invention optionally comprise an assay standard or a set of assay standards, either separately or together with other reagents. An assay standard can serve as a normal control by providing a reference level of normal expression for a given marker that is representative of a healthy individual. In some embodiments, assay standards are not required, as relative numbers of positive cells within a sample will suffice.

A representative example of a kit useful in carrying out the methods described herein comprises: (a) a set of capture antibodies, wherein the capture antibodies specifically bind asialoglycoprotein receptor (ASGPR), Glypican-3, and epithelial cell adhesion molecule (EpCAM); and (b) an antibody that specifically binds vimentin. Optionally, the kit further comprises: (c) a surface to which the set of capture antibodies are bound.

EXAMPLES

The following examples are presented to illustrate the present invention and to assist one of ordinary skill in making and using the same. The examples are not intended in any way to otherwise limit the scope of the invention.

Example: Multimarker Assay for the Phenotypic Profiling of Circulating Tumor Cells in Hepatocellular Carcinoma This Example demonstrates a novel "liquid-biopsy" assay capable of detecting HCC circulating tumor cells (CTCs), and characterizing phenotypic subpopulations with prognostic significance. Utilizing HCC cell lines, a tissue microarray, and human blood samples, an antibody cocktail targeting the cell-surface markers asialoglycoprotein receptor (ASGPR), Glypican-3, and epithelial cell adhesion molecule (EpCAM) was optimized for HCC-CTC capture utilizing the NanoVelcro microfluidic assay. The ability of HCC-CTCs and vimentin(+)-CTCs (a subpopulation expressing an epithelial-to-mesenchymal phenotype) to accurately discriminate tumor stage, recurrence, progression, and overall survival was evaluated in a prospective study of 80 patients.

Hepatocellular carcinoma (HCC) is the fifth most common cancer and the second most common cause of cancer related death worldwide. (1) Unfortunately, current clinicopathologic staging systems and serum biomarkers (e.g. alpha-fetoprotein, AFP) poorly discriminate both early-stage patients amenable to curative-intent surgical resection and liver transplantation (LT), where postoperative recurrence remains a significant challenge, and advanced-stage patients receiving chemotherapy, where predictors of response remain unavailable. (2,3) Thus, the development of better biomarkers to aid in prognostication and treatment selection is an urgent, unmet need.

Circulating tumor cells (CTCs) are thought to originate from the primary tumor or metastatic sites, can be detected in the peripheral blood, and are implicated as a potential cause of post-surgical recurrence and metastases. (4,5) While CTCs can serve as prognostic biomarkers in solid tumors, studies evaluating CTCs in HCC have found limited utility. (6,7) One reason is that most CTC enrichment assays, including the FDA-approved CellSearch™ CTC assay, rely on the use of antibodies against the epithelial cell-surface marker EpCAM to "capture" CTCs by antigen-specific immunomagnetic separation from leukocytes. As only 20-35% of HCCs express EpCAM, methods based on EpCAM alone have resulted in low CTC detection rates and limited utility for HCC. (8) Alternative CTC capture methods utilizing antibodies directed at hepatocyte-specific cell-surface markers (7,9), CD45-depletion (10), or microfluidic (11) systems have all demonstrated increased efficiency in isolating HCC-CTCs. Furthermore, these non-EpCAM based methods allow for capture of distinct CTC subpopulations with more mesenchymal properties in HCC. (9,12)

The identification and significance of CTC subpopulations expressing a mesenchymal phenotype is an area of active investigation in many solid tumors due to their potential role in metastasis. (13) Previous studies in HCC have demonstrated that epithelial-to-mesenchymal transition (EMT), associated with losing expression of cell-cell adhesion markers and gaining the migratory and invasive properties of a mesenchymal cell, is an important step in the metastatic cascade. (14) Several studies in HCC have demonstrated that the overexpression of mesenchymal markers such as vimentin, an intermediate filament, is associated with more advanced tumors and worse prognosis. (15,16) Thus, identifying CTCs that demonstrate an EMT phenotype holds promise for identifying patients likely to harbor aggressive underlying disease.

This study investigated the use of a microfluidic, antibody-based CTC capture assay to efficiently capture HCC-CTCs and characterize CTC phenotypes of prognostic importance. Unlike existing technologies, the NanoVelcro CTC assay combines a microfluidic system with enhanced topographic interactions and CTC-capture antibody coated nanostructured substrates to allow for the efficient separation and capture of HCC-CTCs from background WBCs. The working principle of the NanoVelcro CTC Assay has been utilized for many solid tumors, including prostate cancer, melanoma, and pancreatic cancer. (17,18) To optimize the use of the NanoVelcro Assay for detecting HCC-CTCs from patient blood, HCC CTC capture and immunostaining antibodies (7,19) were investigated, followed by validation of their efficacy using a HCC tissue microarray (TMA), HCC cell lines, and a pilot group of HCC patients. Subsequently, utilizing this optimized assay in a prospective study of patients with non-malignant liver disease (NMLD), HCC patients and healthy controls without HCC or other identified liver disease, the study 1) identified, characterized, and enumerated HCC-CTCs and the subpopulation of vimentin (+)-CTCs, 2) evaluated their ability to discriminate between non-HCC and HCC patients, as well as early-stage and advanced-stage HCC patients, and 3) evaluated their prognostic utility for cancer progression, recurrence, and survival.

Materials and Methods

Antibody Selection for the Capture and Identification of HCC-CTCs

Figure 1:
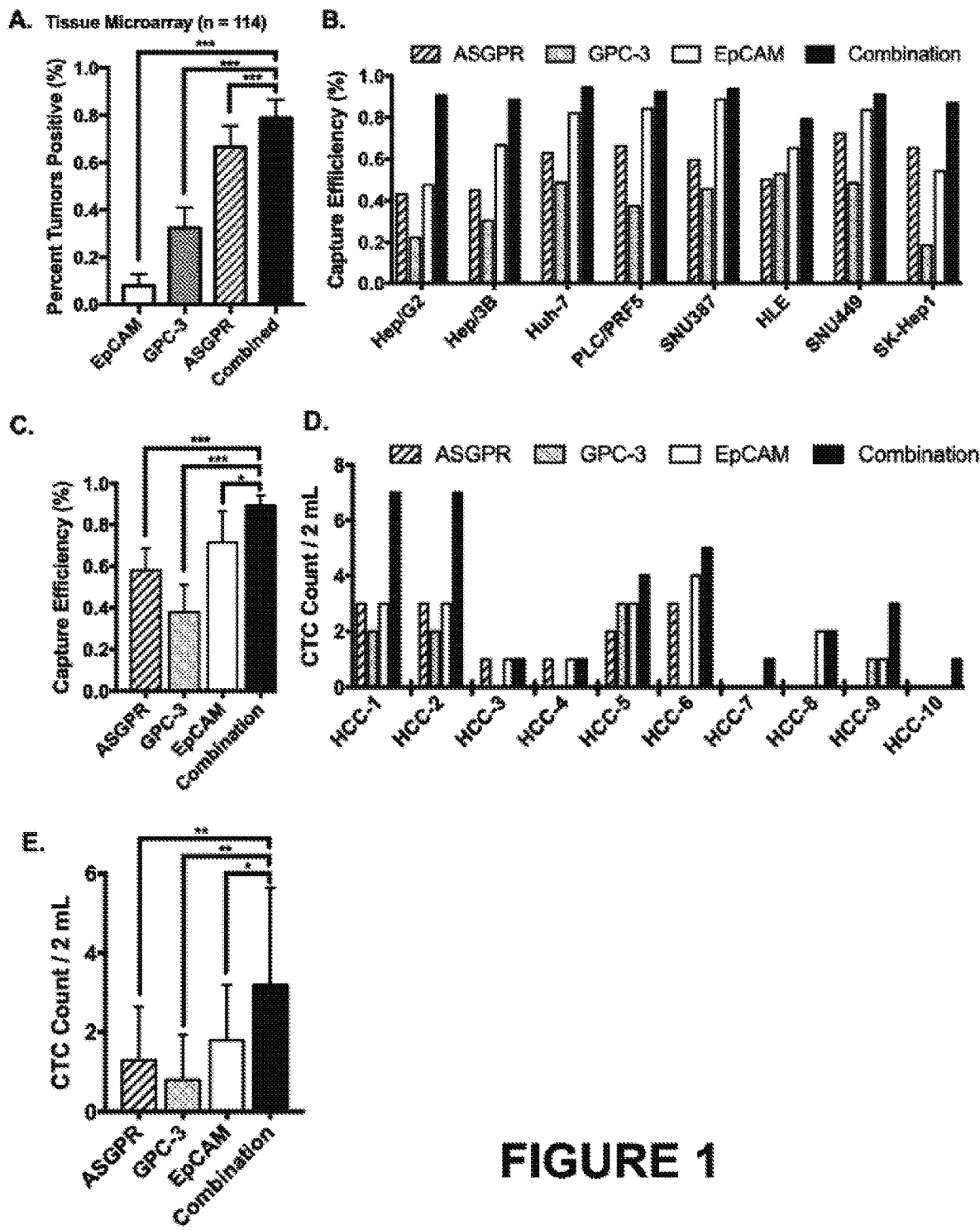
FIG. 1. (A) A 114-tumor tissue microarray was used to test antibodies against markers of interest for the study. Percentage of tumors with moderate to strong staining for the given cell surface marker is shown and compared with the percentage of tumors staining for at least 1 of the 3 markers (Combined). (B) Capture efficiency of the NanoVelcro CTC capture assay using 8 HCC cell lines. Each individual antibody, as well as the multimarker combination of all 3 antibodies, was compared. The percentage of spiked cells that were captured and identified is reported. (C) Summary of capture efficiency data from (B) all 8 cell lines. The combination of all 3 antibodies demonstrated superior capture efficiency compared with the use of any single individual antibody alone. (D) Capture efficiency of NanoVelcro chips functionalized with each antibody individually as well as with the combination of all 3 antibodies for pilot study patient samples (n=10). (E) Summary of capture efficiency data from (D) for each cell surface antibody demonstrating superior capture with the combination of all 3 antibodies (vs. each antibody alone, p<0.05). *—P<0.05; **—P<0.001

The capture of CTCs relies on the antigen-specific immobilization of CTCs on the NanoVelcro surface using antibodies directed against HCC cell surface markers. Immobilized CTCs are then identified and phenotyped based on their immunohistochemical staining characteristics (FIG. 7). A wide selection of antibodies for both CTC capture, as well as CTC identification and phenotyping, were evaluated using an 8 HCC cell line panel as detailed in the supplemental methods. Antibodies demonstrating optimal staining and specificity across the cell line panel were then tested for suitability on a 114-patient HCC tissue microarray (TMA) generated from archived, resected HCC specimens at the University of California, Los Angeles. (20) Antibodies against the cell-surface markers EpCAM (Cell Signaling, Danvers, Mass.), asialoglycoprotein-receptor (ASGPR; Abcam, Cambridge, UK), and glypican-3 (GPC-3; Santa Cruz Biotechnology, Santa Cruz, Calif.), as well as the cytoplasmic marker vimentin (Abcam), were used to stain the TMA (FIG. 8). Staining intensity was assessed on a 4-point scale (none/weak/moderate/strong staining) by a single pathologist (S.W.F.), and tumors were considered to have stained positive if they displayed moderate or strong staining to any one of the antibodies tested (FIG. 9). TMA staining results were summarized as shown in FIG. 1A.

Optimization of Multimarker CTC Capture

The NanoVelcro CTC assay utilizes a microfluidic chaotic mixer to enhance CTC interactions with the capture antibody coated nanosubstrate surface of the chip to enhance CTC capture rates (FIG. 7A). Following CTC capture, CTCs are immunostained as outlined in our workflow (FIG. 7B) and then identified and phenotyped using multi-color ICC and cytometric assessment (FIGS. 10 & 11). While the performance of the NanoVelcro CTC assay has been reported for many solid tumors, we first validated the methodology for HCC using cell lines as previously described and detailed in the supplemental methods. (21) All experiments were performed at the optimum flow rate of 1 mL per hour. (FIG. 12A). Calibration experiments using both HCC cell lines (FIGS. 7B&C) and HCC patient samples (FIGS. 7D&E) were performed to compare the efficiency of the multimarker capture cocktail (EpCAM, ASGPR, GPC-3) to each antibody individually. Cell spiking experiments confirmed the capture efficiency of the assay for CTC concentrations as low as 10 cells in 2 mL of blood (FIG. 12B). For calibration experiments, only 2 mL of blood was utilized; however, for clinical specimens all assays were run as parallel duplicate samples. Thus, CTC counts are recorded per 4 mL of blood except as noted otherwise.

Patient Recruitment and Blood Collection

Between April 2015 and September 2016, healthy controls, patients with non-malignant liver disease (NMLD—cirrhosis without HCC, adenoma, focal nodular hyperplasia), and patients with HCC were enrolled (IRB #14-001932). Inclusion criteria included pathologic or radiographic (LIRADS-5) diagnosis of HCC, with patients having synchronous or past (within 5 years) extrahepatic malignancies excluded from enrollment. A database of demographic and clinicopathologic information was maintained prospectively, with clinical staging assigned based on either pathologic (when available) or radiographic assessment (Milan criteria [MC] (22) and University of California, San Francisco [UCSF] (23) transplant criteria) (Table 1) at study enrollment. Patients were categorized as early-stage if their tumors were within UCSF transplant criteria, locally-advanced if they were outside of UCSF but without extrahepatic disease, and metastatic if there was evidence of distant metastases. The modified Response Evaluation Criteria In Solid Tumors (mRECIST) guidelines were used to evaluate patient's disease status as stable or progressing. (24)

TABLE 1

Radiologic size and additional criteria used to determine transplant eligibility for patients with HCC in the Milan and UCSF criteria.

| | Milan Criteria | UCSF Criteria |
|---|---|---|
| Size | Single lesion ≤5 cm or up to 3 lesions all ≤3 cm | Single lesions ≤6.5 cm or 2-3 lesions ≤4.5 cm and a total tumor diameter ≤8 cm |
| Additional Criteria | No vascular or extrahepatic involvement | No vascular or extrahepatic involvement |

Sample Processing, Chip Scanning and CTC Enumeration

Blood samples were processed as previously described and detailed in the supplemental methods using the parameters determined by the optimization experiments described above. Captured CTCs were imaged using immunocytochemistry (ICC), allowing for both cytometric and immunofluorescent identification parameters, and criteria for CTC identification were developed by a trained cytopathologist (M.S.). Our ICC and cytometric criteria for CTC identification were optimized for HCC-CTCs using the methods described in the supplemental methods and presented in FIGS. 10 and 11. When analyzing the multi-channel ICC image, WBCs were defined as round/ovoid cells, DAPI+/CD45+/CK−, with size ≤6-μm; and HCC-CTCs are defined as round/ovoid cells, DAPI+/CD45−/CK+, with size ≥6-μm. Epithelial-to-mesenchymal phenotype, vimentin(+)-CTCs are the subpopulation of HCC-CTCs defined as round/ovoid events, DAPI+/CD45−/CK+/vimentin+, with size ≥6-μm. Any CD45 positivity greater than 2× background discounted a cell as being a CTC. CTCs were enumerated by the same blinded researcher (S.H.) and CTC counts are represented as a total count per 4-mL VB (FIG. 2B).

Statistical Methods

Continuous variables were summarized as medians and interquartile ranges (IQR) and compared using the Wilcoxon rank sum test, while categorical variables were summarized as frequencies and percentages and compared using the $\chi 2$ test/Fisher exact test. A two tailed p-value <0.05 was considered to be statistically significant. Differences in staining efficiency and CTC capture for different markers were compared using the Wilcoxon matched-pairs signed rank test. CTC enumeration was reported per 4-mL of blood except as otherwise noted, and compared among groups utilizing the non-parametric Mann-Whitney U-test. Cutoff points for CTC enumeration was evaluated using Youden's J statistic and using the cutoff finder web application.25 Diagnostic performance of CTCs was evaluated using receiver operating characteristic curves (ROCs) for determination of the area under the curve (AUROC) in addition to sensitivity, specificity, positive predictive value (PPV), and negative predictive value (NPV) calculations. Outlier analysis was performed with the Iterative Grubb's method (☐=0.05). Outlier analysis did not result in any changes in the statistical interpretation of the results (data not shown).

Both CTC counts and AFP values had a skewed distribution and were log transformed. Post-transplant patients without a pre-transplant blood draw were not included in the survival analysis (n=1). Overall survival (OS) was the time from initial blood draw (study enrollment) to last follow-up or death, with only death counting as an event. Progression-free survival (PFS) was evaluated only in the subset of advanced stage, incurable patients, with progression defined as measurable radiographic increase in tumor burden (measured by mRECIST), and measured from time of study enrollment to first radiographic progression or cancer-related death. Time to recurrence (TTR) was evaluated only in the subset of early stage, potentially curable patients undergoing curative intent surgical or locoregional therapy, where the initial post-treatment imaging showed no viable arterially enhancing lesions (irrespective of surgical resection, ablation, or in select cases, TACE treatment). Recurrence was defined as a new or recurrent radiographic lesion meeting OPTN criteria for HCC. Time to recurrence (TTR) of radiographically evident disease, progression-free (PFS), and overall survival (OS) were computed using Kaplan-Meier methods and compared by the log-rank (Mantel-Cox) test.

Univariate analysis of individual predictors of PFS and TTR was performed using the Fine and Gray competing risks Cox regression model to account for the competing risk of non-HCC related mortality. Factors identified as significant (p<0.2) on univariate analysis were entered in to a multivariate competing risk Cox regression model to identify significant independent predictors of HCC progression and recurrence. Hazard ratios and 95% CIs were reported and statistical significance assessed based on non-overlapping 95% CIs. For multivariate analysis, final models for OS, PFS, and TTR included AFP, UCSF staging, and primary tumor size, in addition to CTC count for both HCC-CTCs and the subpopulation of vimentin(+) CTCs. The hazard ratios reported are per standard deviation increase (SD increase) of the CTC count on the log-scale. All statistical analyses and calculations were performed with the assistance of GraphPad Prism 7.0a (GraphPad Software, La Jolla, Calif.) and SAS (SAS Institute, Cary, N.C.), and follow the REporting recommendations for tumor MARKer prognostic studies (REMARK) guidelines. (26)

Cell Culture

Hepatocellular carcinoma cell lines (HepG2, Hep3B, Huh-7, PLC/PRF/5, SNU-387, HLE, SNU-449, SK-Hep-1, and MCF-7) were obtained from American Type Culture Collection (ATCC, Manassas, Va.), grown using ATCC recommended media at 37° C. with 5% $CO_2$, and routinely passaged at 80% confluence using an iso-osmotic sodium citrate solution for cell release (Thermo Fisher Scientific, Waltham, Mass.). The cell lines were specifically selected to ensure a broadly representative class of HCC cells with varying phenotypes, differentiation, sites of origin, and cell surface marker expressions (Table 2).

TABLE 2

Original source, phenotypic features, protein expression levels, and growth medium for cell lines used in the study.

| Cell Line | Hep G2 | Hep 3B | Huh-7 | PLC/PRF/5 | SHU-387 | HLE | SNU-449 | SK-Hep-1 |
|---|---|---|---|---|---|---|---|---|
| Source | Liver | Liver | Liver | Liver | Liver | Liver | Liver | Ascites |
| Differentiation | Well | Well | Well | Well | Pleomorphic | Poor | Poor | Poor |
| Phenotype | Epithelial | Epithelial | Epithelial | Mixed | Mixed | Mesenchymal | Mesenchymal | Mesenchymal |
| HBV | + | + | − | + | + | − | + | + |
| AFP | + | + | + | + | − | + | − | − |
| EpCAM expression | Med | Med | High | Bimodal | Low | Low | Low | Bimodal |
| CK expression | Med | Low | Med | Low | NA | NA | NA | Med |
| ASGP expression | Low | Low | High | NA | NA | NA | NA | Med |
| GPC3 expression | Low | Low | Med | NA | NA | NA | NA | Low |
| Growth Medium | EMEM | EMEM | DMEM | DMEM | RPMI | DMEM | RPMI | DMEM |

Selection of Capture and Phenotyping Antibodies

We created a cell line panel consisting of 8 HCC cell lines with varying phenotypes, differentiation, sites of origin, and cell surface marker expressions (Table 2). (1-3) We used our cell line panel to test both antibodies against HCC-specific cell surface markers for CTC capture, as well as antibodies directed at intracellular markers of epithelial or mesenchymal differentiation for CTC phenotyping. For each antibody, staining was optimized using serial dilutions, and staining intensity for each of the cell lines assessed by a trained cytopathologist (M.S.). Both relative antigen expression and appropriateness for study inclusion were evaluated and quantified. Based on the results of these staining experiments, antibodies against EpCAM (Abcam, Cambridge, UK; R&D Systems, Minneapolis, Minn.), ASGPR (Abcam), glypican-3 (GPC-3, R&D), CD45 (Abcam; DAKO, Glostrup, DK), CK (DAKO; Abcam), and vimentin (Abcam) were chosen for CTC capture and phenotyping experiments. Antibodies for CTC capture were either purchased in a biotinylated form from the manufacturer or were biotinylated using the EZ-Link™ NHS-PEG Solid-Phase Biotinylation Kit (Life Technologies, Grand Island, N.Y.) using the manufacturers recommended protocol.

Tissue Microarray Staining

Cell surface marker antibodies against EpCAM (Cell Signaling, Danvers, Mass.), ASGPR (Abcam), and GPC-3 (Santa Cruz Biotechnology, Santa Cruz, Calif.) were used to stain the TMA using the EnVision™+Dual Link Kit (DAKO) according to the manufacturer's protocol (FIG. 7). Cytoplasmic antibodies of interest to the study, primarily vimentin (Abcam), were also tested using the same protocol as for the cell surface markers. Staining intensity was assessed on a 4-point scale (1-none, 2-weak, 3-moderate, and 4-strong staining) by a single pathologist (S.W.F.) (FIG. 8). For all antibody markers, tumors demonstrating moderate or strong staining (3 or 4 on a 4 point scale) were considered to be positive for that marker.

Optimization of Multimarker CTC Capture Utilizing the Microfluidic NanoVelcro Assay For the initial calibration experiments, 500 cells from each of the cell lines were first incubated with CTC capture antibodies. After briefly washing, the pre-labeled HCC cell line cells were spiked into 2-mL healthy donor blood to create artificial blood samples. Artificial blood samples were run in triplicate at flow rates of 0.1, 0.5, 1.0, 2.0, and 3.0 mL/h using 8 of the HCC cell lines (Hep-G2, PLC/PRF5, Huh-7, Hep-3B, SNU387, HLE, SNU449, and SK-Hep1). CTC capture efficiency, defined as the fraction of CK+/CD45-CTCs captured and identified over the known total number of spiked cells, was maximized at a flow rate of 1.0 ml/h (FIG. 12). This optimized flow rate was used for all subsequent experiments. The capture antibodies used, either individually or in combination, did not substantially affect the optimum flow rate of 1 mL per hour.

Optimization of Multimarker CTC Capture Utilizing the Microfluidic NanoVelcro Assay Based on the results of the cell line and TMA staining, the triple antibody cocktail of EpCAM, ASGPR, and GPC-3 was assessed for CTC capture efficiency. Using the protocol outlined in Sample Processing below, each of the 8 HCC cell lines were run on 4 NanoVelcro chips: one chip for each individual antibody with the fourth assay evaluating the combination of all 3 antibodies simultaneously. The cell capture efficiencies were compared to determine the optimum capture antibody cocktail (FIGS. 1B&C).

To ensure that our cell line optimization held true for patient HCC samples, we investigated CTC enumeration for the antibody cocktail versus each capture antibody individually for 10 patients. Four NanoVelcro chips were prepared, one for each antibody and one for the antibody cocktail (EpCAM, ASGPR, GPC-3). A total of 2 mL of blood was processed on each of the 4 chips and the CTC counts recorded as outlined below in the Sample Processing section (FIGS. 1D&E).

Blood Collection and Sample Processing

Following discard of 5 mL of venous blood (VB) to prevent epithelial contamination, 10 mL of VB was collected into ACD solution A tubes (BD-Pharmigen, Franklin Lakes, N.J.), and stored at 4° C. until processed. All samples were processed within 24 hours of collection. Mononuclear cells were isolated from the blood samples by density gradient centrifugation. Blood samples were first diluted 1:1 with PBS (Sigma, St. Louis, Mo.) and transferred to 12 mL LeucoSep centrifuge tubes (VWR, Radnor, Pa.) with 3 mL of Histopaque-1077 (Sigma) below the porous barrier. Samples were centrifuged at 400×g at 4° C. for 30 minutes with the break off. The buffy coat layer was then transferred to a new 15 mL tube and washed with 5 mL of wash medium (RPMI with 5% FBS, Gibco, Carlsbad, Calif.), centrifuged at 300×g for 10 minutes at 4° C., and the pellet resuspended in 200 µL of PBS supplemented with 2% donkey serum (DS). 6 µL of biotinylated capture antibody cocktail (EpCAM, ASGPR, GPC-3) was added and the mixture was incubated on a shaker for 30 minutes at room temperature. Following a final wash step, the pellet was re-suspended in 200 µL of PBS and immediately processed on the NanoVelcro platform.

NanoVelcro Chip Preparation, Immunocytochemistry and Chip Mounting

NanoVelcro chips were assembled and operated as previously described. (4) Prepared samples were injected into the device at the optimized flow rate of 1.0 mL/h, followed by 4% paraformaldehyde (PFA) injected at the same rate for fixation. The chips were then removed from the NanoVelcro platform and washed in PBS for 15 minutes. Chips were blocked and permeabilized using PBS+2% DS+0.1% Triton X-100 (Sigma) for 15 minutes. Chips were then incubated with a cocktail of primary antibodies including two mouse anti-CD45 antibodies (DAKO, Abcam), two rabbit anti-cytokeratin (CK) antibodies (DAKO, Abcam) and 1 chicken anti-vimentin antibody (Abcam). Primary antibody incubation occurred for 1 hour at room temperature in PBS+2% DS. Following a wash step using PBS, secondary antibody incubation was performed with a cocktail of AlexaFluor-488 donkey anti-rabbit (Invitrogen, Carlsbad, Calif.), AlexaFluor-647 goat anti-chicken (Invitrogen), and AlexaFluor-555 donkey anti-mouse (Invitrogen). Secondary antibody incubation was carried out in PBS+2% DS for 1 hour at room temperature. Chips were washed a final time with PBS and then attached to microscope slides (Fisher Scientific, Waltham, Mass.). A DAPI mounting solution (Life Technologies, Grand Island, N.Y.) was used to mount cover slips, and mounted slides were dried for 1 hour prior to fluorescent imaging.

Chip Scanning and CTC Enumeration

Chips were first scanned at 40× power by an automated chip scanning protocol using the NIS Elements 4.1 software (Nikon, Tokyo, Japan) on an Eclipse 90i fluorescent microscope to identify candidate cells. Higher magnification manual imaging of candidate cells was then performed at 400× power to verify results. When analyzing the resulting multi-channel ICC image, WBCs were defined as round/ovoid, DAPI+, CD45+ and CK−. CTCs were defined as round/ovoid, size ≥6-µm, DAPI+, CD45−, and CK+ and/or vimentin+. Any CD45 positivity greater than 2× background discounted a cell as being a CTC. Final CTC counts are represented as a total count per 4 mL VB.

Results

Antibody Selection for the Capture and Identification of HCC-CTCs

CTCs are first incubated with biotinylated antibody cocktail (EpCAM, ASGPR, GPC-3) and then "captured" by the NanoVelcro assay through the interaction of biotin on the CTCs with the streptavidin-coated surface of the NanoVelcro chips. To optimize CTC capture we utilized a TMA developed from 114 resected human HCC samples to screen the potential HCC-specific cell-surface capture markers ASGPR and GPC-3, in addition to the widely-utilized cell-surface marker EpCAM. Of the 114 tumors, 89 (78.9%) stained for at least 1/3 antibodies (ASGPR-65.8%, GPC-3-31.6%, EpCAM-7.9%, Fig. A). However, the combination of all 3 antibodies stained significantly more tumors than any single antibody alone for the entire TMA, with staining of any one or more of the antibodies considered positive ($p<0.001$ for ASGPR alone and $p<0.001$ for EpCAM or GPC-3 alone).

Optimization of the NanoVelcro CTC Assay utilizing multimarker CTC Capture

Capture Antibody Optimization in HCC Cell Lines

Utilizing artificial blood samples consisting of 500 HCC cell line cells spiked in 2 mL normal blood samples, the CTC capture efficiency for each individual capture antibody (EpCAM, ASGPR, GPC-3) was compared to the combination of all 3 antibodies for 8 HCC cell lines (FIG. 1B). Use of the triple-antibody multimarker capture cocktail resulted in the highest CTC capture efficiency (>80%), significantly greater than any single capture antibody alone ($p=0.018$ for EpCAM, $p<0.001$ for ASGPR and GPC-3, FIG. 1C).

Capture Antibody Optimization in Human HCC Patients

In a preliminary cohort of 10 patients with HCC, we evaluated the total CTCs enumerated using EpCAM alone, ASGPR alone, GPC-3 alone, and the triple multimarker antibody cocktail (FIG. 1D). Similar to our cell line results, we found that the combination of all 3 capture antibodies resulted in significantly greater CTCs captured compared with the use of any single antibody alone (vs. multimarker capture, p=0.041 for EpCAM, p=0.007 for ASGPR, and p=0.007 for GPC-3, FIG. 1E).

Defining HCC-CTC Phenotypes

To ensure that our immunocytochemical staining of HCC-CTCs was specific for hepatocytes, selected patient samples were stained with CK as the primary epithelial marker, and co-stained with hepatocyte-specific markers AFP, arginase, and hep-par-1. AFP, arginase, and hep-par-1 staining was only noted in the CK+ cells and never in the CD45+ leukocytes, confirming the specificity of our ICC criteria for HCC-CTCs (FIG. 11). Additionally, we discovered a subpopulation of vimentin(+) CTCs with an epithelial-to-mesenchymal phenotype. Based on these initial experiments, all prospective HCC patients enrolled in the study underwent enumeration of HCC-CTCs and the subpopulation of vimentin(+)-CTCs (FIG. 2).

Prospective Study Evaluating CTC Enumeration and Phenotype Utilizing Optimized Multimarker HCC NanoVelcro Assay Of 84 patients approached for study participation, 80 patients underwent peripheral blood draw, CTC enumeration, and phenotyping using our optimized multimarker NanoVelcro HCC-CTC assay (Table 3). Four patients were excluded (2-refused informed consent, 1-synchronous cancer, 1-insufficient blood draw). Of the 80 enrolled patients, 61 had HCC, 11 had NMLD (7-cirrhosis without HCC, 4-benign liver lesions), and 8 were healthy controls (FIG. 3). Among patients with HCC, 31/61 (50.8%) were early-stage (within UCSF transplant eligibility criteria), 23 21/61 (34.4%) were locally-advanced with extensive liver involvement, and 9/61 (14.8%) were metastatic. Overall, 41% of enrolled patients received prior systemic or locoregional therapy (median 124 days, range 23-235 days prior to blood draw). Patients were followed for a median of 325 days after blood draw. Of the 61 patients with HCC, 28 (45.9%) progressed and 20 (32.8%) died. Patients with NMLD were followed for an equivalent amount of time. None of the NMLD or healthy control patients involved in the study developed HCC during follow-up.

TABLE 3

Clinical, Laboratory, Radiologic, and Treatment Characteristics of the Prospective Cohort (n = 80)

| Characteristics | Data |
|---|---|
| Age, median (IQR) | 61 (53-68) |
| Female, n (%) | 23 (28.8) |
| Diagnosis, n (%) | |
| HCC | 61 (76) |
| Healthy | 8 (10) |
| Cirrhosis | 7 (9) |
| Adenoma | 4 (5) |
| Laboratory | |
| Physiologic MELD, median (IQR) | 8 (7-13) |
| Childs Class, n (%) | |
| A | 60 (75) |
| B | 9 (11.5) |
| C | 11 (13.8) |
| Most recent AFP, median (IQR) | 24 (5-790) |
| Maximum pre-draw AFP, median (IQR) | 38 (7-1148) |
| HCC Cause, n (%) | |
| HCV | 40 (65.6) |
| HBV | 11 (18) |

TABLE 3-continued

Clinical, Laboratory, Radiologic, and Treatment Characteristics of the Prospective Cohort (n = 80)

| | Data |
|---|---|
| NASH | 5 (8.2) |
| Other | 3 (4.9) |
| Unknown/non-cirrhotic | 2 (3.3) |
| Radiologic | |
| Maximum tumor diameter, median (IQR) | 4.6 (3.4-6.7) |
| Cumulative tumor diameter, median (IQR) | 6.2 (3.5-9.7) |
| Predraw treatment characteristics | |
| Any predraw treatment, n (% of all HCC) | 25 (41.0) |
| Early stage (within UCSF) | 8 (32.0) |
| Advanced stage (outside UCSF) | 17 (68.0) |
| No. of predraw treatments, n (% of treated pts) | |
| 1 | 12 (48) |
| 2 | 2 (8) |
| 3 | 5 (20) |
| 4+ | 6 (24) |
| Type of treatment, n (% of treated pts) | |
| Sorafenib | 10 (40) |
| Nivolumab | 4 (16) |
| Other systemic therapy | 1 (4) |
| Radioembolization (Y90) | 2 (8) |
| Transarterial chemoembolization (TACE) | 12 (48) |
| Thermal ablation | 9 (36) |
| Transplant criteria | |
| Within Milan criteria, n (%) | 23 (37.7) |
| Outside Milan, within UCSF criteria, n (%) | 8 (13.1) |
| Outside UCSF criteria/locoregional only, n (%) | 21 (34.4) |
| Metastatic disease, n (%) | 9 (14.8) |
| BCLC stage | |
| A | 11 (18) |
| B | 17 (27.9) |
| C | 26 (42.6) |
| D | 7 (11.5) |

IQR—interquartile range,
HCC—hepatocellular carcinoma,
MELD—Model for End-Stage Liver Disease,
AFP—alphafetoprotein,
HCV—hepatitis C virus,
HBV—hepatitis B virus,
NASH—Nonalcoholic steatohepatitis,
BCLC—Barcelona clinic liver cancer stage HCC-CTCs HCC-CTCs were found in 59/61 (96.7%) patients with HCC (median=6, range=0-23). Occasional patients with NMLD were found to have low numbers of CTCs (median: 1, range:0-7), particularly those with inflammatory adenomas (FIG. 2B). A single CTC was found in 2/8 (25%) healthy control patients, indicating a false positive. Among patients with HCC, CTC count correlated with stage, with a median of 3 CTCs in early stage patients (range:0-15), 9 CTCs in locally advanced HCC (range:0-14), and 12 CTCs in patients with metastatic HCC (range:2-23) (FIG. 3). Significantly more HCC-CTCs were found in patients with radiographic evidence of portal vein invasion (p=0.001).

At the optimum cutoff of ≥2 CTCs/4 mL VB, HCC-CTC enumeration accurately discriminated among patients with and without HCC (NMLD or healthy controls) with a sensitivity=84.2%, specificity=88.5%, PPV=69.6%, NPV=94.7% (FIG. 4A) and an area under the ROC curve (AUROC) of 0.92 (95% CI=0.86-0.99, p<0.001), illustrating the ability of CTCs to discriminate patients with cancer from those without (FIG. 4B). A similar discriminatory performance was found when HCC patients were compared to NMLD alone (AUROC=0.89).

Univariate Cox analysis of all HCC patients revealed that HCC-CTCs were associated with worse OS (HR:1.96, 95% CI: 1.12-3.42, p=0.018). In the subset of non-metastatic, potentially curable patients (n=30) who underwent locoregional therapy (resection, n=9; transplantation, n=5; RFA, n=11; or TACE, n=5), HCC-CTCs were associated with faster TTR (HR: 9.7, 95% CI: 2.08-45.19, p=0.004). In patients with incurable, locally advanced (n=15, diffuse infiltration or macrovascular invasion) or metastatic disease (n=8), HCC-CTCs were associated with worse PFS (HR: 2.09, 95% CI: 1.11-3.96, p=0.023). On multivariate analysis, including the covariates age, AFP, MELD score and tumor size, HCC-CTCs were again found to be significantly associated with PFS (HR: 2.09, 95% CI: 1.11-3.96, p=0.023) in the subset of advanced stage patients, but not TTR in potentially curable early stage patients or OS in all patients.

Vimentin(+)-CTCs

Vimentin(+) CTCs were found in 31 (50.8%) patients with HCC (median:1, range:0-20) and never in patients with NMLD or healthy controls (FIG. 4C). Among HCC patients, the number of vimentin(+)-CTCs correlated with increasing tumor stage, with only 4/31 (12.9%) early stage patients demonstrating vimentin(+)-CTCs (median:0, IQR:0-0, range:0-12), compared to 18/21 (85.7%) locally advanced patients (median:4, IQR:2-6, range:0-8), and 9/9 (100%) metastatic HCC patients (median:8, IQR:8-14, range:1-20). Significantly more vimentin(+)-CTCs were found in patient with radiographic evidence of portal vein invasion (p<0.001).

At a cutoff of ≥1 CTC/4 mL VB, vimentin(+)-CTCs accurately discriminated transplant eligible HCC patients with early stage, potentially curable disease from transplant ineligible patients with locally advanced or metastatic HCC (FIG. 4C), with a sensitivity=87.1%, specificity=90.0%, PPV=90.0%, NPV=87.1%, and an AUROC of 0.89 (95% CI: 0.74-0.95, p<0.0001) (FIG. 4D), significantly superior to the AUROC of HCC-CTCs (AUROC 0.55; 95% CI: 0.47-0.63; p<0.001) in discriminating early and advanced stage HCC. For additional comparisons, we performed the same analysis for AFP, the only widely available HCC biomarker. AFP discriminated early stage from advanced stage disease with a sensitivity=93.5%, specificity=46.7%, PPV=65.6%, NPV=65.5%, and AUROC of 0.66 (95% CI=0.53-0.78, p=0.021). Thus, vimentin(+)-CTCs were a significantly better predictor of advanced stage disease than AFP (DeLong's-test, Z=2.6, p=0.009).

Univariate analysis of all HCC patients revealed that vimentin(+)-CTCs were highly associated with inferior OS (HR: 2.21, 95% CI: 1.38-3.52, p=0.001) (FIG. 5A). Perhaps more notably, CTCs were able to discriminate outcomes in the subset of potentially curable patients undergoing locoregional therapy (resection, n=9; transplantation, n=5; RFA, n=1, and TACE, n=5). In this subset of 30 patients who radiographically demonstrated no residual disease following treatment, the presence of any pre-treatment vimentin(+)-CTCs were associated with faster TTR (HR:3.14, 95% CI: 1.50-6.57, p=0.002) (FIG. 5B). Similarly, in the subset of incurable locally advanced or metastatic patients (n=23), vimentin(+)-CTCs were predictive of worse PFS (HR:1.81, 95% CI: 1.02-3.22, p=0.043) (FIG. 5C). On multivariate analysis, vimentin(+)-CTCs were found to be significantly associated with OS (HR:2.21, 95% CI: 1.38-3.56, p=0.001) in all patients, PFS (HR:2.16, 95% CI: 1.33-4.42, p=0.002) in the subset of advanced stage, incurable patients, and with a trend towards faster TTR (HR:2.45, 95% CI: 0.91-6.57, p=0.076) in the subset of early stage, potentially curable patients undergoing surgical or locoregional therapy.

Potential Utility of HCC-CTCs

The value of HCC-CTCs and vimentin(+)-CTCs as biomarkers goes beyond initial prognosis, presenting potential utility for both longitudinal disease monitoring as well as appropriate treatment selection. 11 patients in the study underwent serial blood draws and CTC enumeration over the course of treatment, with disappearance of CTCs following successful tumor resection and ablation, and a subsequent reappearance of CTCs prior to clinical recurrence (data not shown). One such example is illustrated in FIG. 6A. The patient was a 63-year-old gentleman with compensated cirrhosis and a 5.8 cm arterially enhancing biopsy-proven HCC. His pre-resection blood draw revealed 8 vimentin(+)-CTCs (14 total HCC-CTCs). He underwent a partial right hepatectomy which revealed a 5.8 cm dominant lesion with a subcentimeter satellite lesion with microvascular invasion. CTC enumeration at 1 and 2 months post-resection revealed no CTCs, with MRI imaging revealing no evidence of recurrence. However, his 3rd post-resection blood draw revealed 6 vimentin(+)-CTCs (12 HCC-CTCs), with subsequent MRI demonstrating a segment 8 HCC recurrence.

The presence of vimentin(+)-CTCs consistently portended faster time to recurrence following locoregional treatment (FIG. 5D), with an example illustrated in FIG. 6B. The patient had a solitary 4 cm right hepatic lobe HCC without evidence of metastases, but despite being radiographically staged as an early stage patient, was found to have 12 vimentin(+) CTCs (15 HCC-CTCs). Despite successful locoregional therapy with TACE, she was found to have multifocal HCC on her 1 month post-procedure scan with rapid development of metastatic lung nodules at 3 months' post-procedure.

DISCUSSION

The limitations of existing clinicopathologic staging systems of HCC is evident in the high recurrence rate following locoregional therapies or curative-intent surgical interventions such as resection or transplantation. CTCs are emerging as a promising biomarker for several cancer types, but their application to HCC has been limited when utilizing existing assays that rely on epithelial cell-surface markers alone for CTC capture. In this study, we present the development of a novel multimarker CTC capture platform that allows for the identification, enumeration, and analysis of HCC-CTCs with high sensitivity and specificity. Furthermore, we identify a phenotypic subpopulation of vimentin(+)-CTCs, which are highly associated with advanced or metastatic HCC, increased recurrence after potentially curative therapy, and inferior progression-free and overall survival.

A unique strength of our study was the utilization of a multimarker capture antibody cocktail that allowed for the detection of CTCs across all HCC stages with high sensitivity and specificity. The majority of current CTC enrichment platforms rely on antibodies to the cell-surface marker EpCAM alone, potentially limiting their utility in HCC where expression of EpCAM is reported in only 20-35% of tumors. (8) ASGPR, a transmembrane cell-surface protein highly expressed in well-differentiated HCCs, yielded high CTC capture rates in previous HCC studies, and was used in our antibody cocktail. (7,9,19) Based on our TMA studies, we also included GPC-3, since its expression has been associated with the presence of poorly-differentiated HCC, 27 arguably the most important subset of tumors to be detected given their poor prognosis. This unique threemarker antibody cocktail allowed us to detect CTCs from 96.7% of all patients with HCC, compared to 20-50% captured using EpCAM alone. (6,28-30)

Arguably our most important finding was the identification of the subpopulation of vimentin(+)-CTCs and their association with more advanced stage disease, faster HCC progression and inferior survival for all patients and the subset of potentially curable patients undergoing locoregional treatments (FIGS. 5A&C). Vimentin is an intermediate filament ubiquitously expressed in normal mesenchymal cells and is involved in cellular processes including stress resistance and structural integrity. (31) Vimentin overexpression is widely regarded as the canonical marker of EMT in epithelial cancers (31), and tumors expressing vimentin demonstrate accelerated tumor growth and increased invasiveness. In HCC, vimentin overexpression in the primary tumor has been linked to more aggressive tumor biology, inferior survival outcomes, and the establishment of the tumor initiating capacity critical for metastases. (14,15)

The importance of vimentin overexpression in CTCs as a marker of metastatic potential has been established previously in several cancer types, but the utility of vimentin for HCC-CTCs has only recently been considered. (13,32-34) The finding that vimentin(+)-CTCs were found almost exclusively in patients with advanced stage HCC corroborates previous reports in breast and prostate cancer that found the presence of vimentin(+)-CTCs as a marker of metastatic disease and worse outcomes. (35) Given that cytokeratin-positive epithelial cells have been found in the blood of patients with inflammatory gastrointestinal disease such as inflammatory bowel disease and cirrhosis, the use of additional markers can ensure that no benign epithelial cells are being mis-identified as CTCs. (36) This is one reason that vimentin(+)-CTCs may hold more clinical relevance for HCC, where the vast majority of patients have underlying liver cirrhosis. Furthermore, vimentin(+)-CTCs vastly outperform the only existing serum biomarker, AFP, for both HCC staging and prognosis (FIG. 4D). In particular, the finding that vimentin(+)-CTCs are highly predictive of earlier recurrence and worse survival in otherwise indistinguishable early stage patients undergoing locoregional or surgical therapy highlights their potential utility as a biomarker for liver transplant candidate selection. Hopefully, the use of vimentin(+)-CTCs as an adjunct biomarker may help overcome the limitation of existing clinicopathologic staging systems in distinguishing cancer-specific outcomes within the subset of potentially curable patients.

This study builds upon recent publications highlighting the potential utility of CTCs, and CTC phenotyping in particular. Wang et al used fluorescent in situ hybridization of mesenchymal and epithelial mRNA transcripts in CTCs to demonstrate that the presence of one or more mesenchymal CTCs was associated with early recurrence after curative-intent resection. (32) Similarly and using the same CTC capture system, Chen et al., found that CTCs can discriminate between patients with metastatic and non-metastatic disease, and that significantly more mesenchymal CTC were found in patients with metastatic disease and higher BCLC stage. (34) These recent studies, along with our current findings, highlight the potential of mesenchymal CTCs, such as vimentin(+)-CTCs, as a clinical biomarker for patients with HCC that may play an important role in prognostication and treatment selection.

The value of HCC-CTCs as a tool for both longitudinal monitoring of disease and identification of patients with aggressive underlying disease is apparent. Given the ease and repeatability of the non-invasive HCC-CTC assay, the reliable serial monitoring of a patient's response to treatment would be possible. In patients undergoing surgical resection and ablation, total HCC-CTCs dropped significantly after treatment, but increased in the subset of patients who subsequently proved to have recurrence on follow up imaging (FIG. 6). In addition, Vimentin(+)-CTCs were highly predictive of recurrence and progression in the subset of potentially curable patients undergoing successful locoregional therapy who initially demonstrated no evidence of disease on post-treatment imaging. This highlights the potential role of vimentin(+)-CTCs for the selection of patients undergoing curative liver transplantation, where the identification of patients likely to have poor outcomes is a critical, unmet need to avoid the loss of scarce donor allografts.

In conclusion, the HCC multimarker antibody-based CTC capture assay described herein allows for the identification of HCC-CTCs as well as a distinct subpopulation of vimentin(+)-CTCs. The study first optimized and validated the assay's functionality for capturing HCC-CTCs using both spiked cell line and clinical samples. In a subsequent prospective study of 80 patients (one of the largest HCC-CTC studies to date), 61 of whom had HCC, the assay allowed for detection of HCC-CTCs from nearly all patients with HCC, with highly accurate discrimination between patients with HCC and those with NMLD or healthy controls. Most importantly, a phenotypic subpopulation of EMT-type, vimentin(+)-CTCs allowed for accurate discrimination of patients with early stage, potentially curable HCC from those with advanced stage, incurable disease. The presence of any vimentin(+)-CTCs was associated with earlier recurrence and inferior progression free survival in the subset of patients undergoing curative intent locoregional therapy. Results indicate that the novel NanoVelcro CTC assay is effective for HCC-CTC capture and phenotyping, with vimentin(+)-CTCs showing great promise for identifying early stage patients with occult aggressive disease.

REFERENCES

1 Lozano, R. et al. Lancet 380, 2095-2128, doi:10.1016/S0140-6736(12)61728-0 (2012).
2 Agopian, V. G. et al. J Am Coil Surg 220, 416-427, doi:10.1016/j.jamcollsurg.2014.12.025 (2015).
3 Uovet, J. M. & Hernandez-Gea, V. Clin Cancer Res 20, 2072-2079, doi:10.1158/1078-0432.CCR-13-0547 (2014).
4 Baccelli, I. et al. Nat Biotechnol 31, 539-544, doi:10.1038/nbt.2576 (2013).
5 Court, C. M. et al. The Journal of molecular diagnostics: JMD 18, 688-696, doi:10.1016/j.jmoldx.2016.03.006 (2016).
6 Fan, J. L., et al. Cell Physiol Biochem 37, 629-640, doi:10.1159/000430382 (2015).
7 Xu, W. et al. Clinical cancer research: an official journal of the American Association for Cancer Research 17, 3783-3793, doi:10.1158/1078-0432.CCR-10-0498 [doi] (2011).
8 de Boer, et al. The Journal of pathology 188, 201-206, doi:10.1002/(SICI)1096-9896(199906)188:2<201::AID-PATH339>3.0.CO;2-8 (1999).
9 U, Y. M. et al. Cell Death Dis 4, e831, doi:10.1038/cddis.2013.347 (2013).
10 Nel, I. et al. Translational oncology 6, 420-428 (2013).
11 Fan, S. T. et al. Annals of Surgery 254, 569-576, doi:10.1097/SLA.0b013e3182300a1d [doi] (2011).
12 Chen, L. et al. Biosensors & bioelectronics 85, 633-640, doi:10.1016/j.bios.2016.05.071 (2016).

13 Yu, M. et al. Science 339, 580-584, doi:10.1126/science.1228522 (2013).
14 Giannelli, G., et al. J Hepatol 65, 798-808, doi:10.1016/j.jhep.2016.05.007 (2016).
15 Hu, L. et al. Oncogene 23, 298-302, doi:10.1038/sj.onc.1206483 (2004).
16 Yang, M. H. et al. Hepatology 50, 1464-1474, doi:10.1002/hep.23221 (2009).
17 Chen, J. F. et al. Cancer, doi:10.1002/cncr.29455 (2015).
18 Lin, M. et al. Accounts of chemical research 47, 2941-2950, doi:10.1021/ar5001617 (2014).
19 Li, J. et al. PoS one 9, e96185, doi:10.1371/journal.pone.0096185 [doi] (2014).
20 Buzzanco, A. et al. Exp Mol Pathol 97, 399-410, doi:10.1016/j.yexmp.2014.09.002 (2014).
21 Ankeny, J. S. et al. Br J Cancer 114, 1367-1375, doi:10.1038/bjc.2016.121 (2016).
22 Mazzaferro, V. et al. N Engl J Med 334, 693-699, doi:10.1056/NEJM199603143341104 (1996).
23 Yao, F. Y. et al. Hepatology 33, 1394-1403, doi:10.1053/jhep.2001.24563 (2001).
24 Lencioni, R. & Llovet, J. M. Semin Liver Dis 30, 52-60, doi:10.1055/s-0030-1247132 (2010).
25 Budczies, J. et al. PLoS One 7, e51862, doi:10.1371/journal.pone.0051862 (2012).
26 McShane, L. M. et al. Journal of the National Cancer Institute 97, 1180-1184, doi:10.1093/jnci/dji237 (2005).
27 Libbrecht, L. et al. Am J Surg Pathol 30, 1405-1411, doi:10.1097/01. pas.0000213323.97294.9a (2006).
28 Schulze, K. et al. Journal international du cancer 133, 2165-2171, doi:10.1002/ijc.28230 [doi] (2013).
29 Sanchez-Lorencio, M. I. et al. Transplant Proc 47, 2639-2642, doi:10.1016/j.transproceed.2015.10.003 (2015).
30 Ogle, L. F. et al. J Hepatol 65, 305-313, doi:10.1016/j.jhep.2016.04.014 (2016).
31 Satelli, A. & Li, S. Cell Mol Life Sci 68, 3033-3046, doi:10.1007/s00018-011-0735-1 (2011).
32 Wang, Z. et al. Journal of gastrointestinal surgery: official journal of the Society for Surgery of the Alimentary Tract, doi:10.1007/sl 1605-017-3619-3 (2017).
33 Lee, H. M. et al. Scientific reports 7, 13201, doi:10.1038/s41598-017-13501-1 (2017).
34 Chen, J., et al. Cancer Biomark 20, 487-498, doi:10.3233/CBM-170315 (2017).
35 Armstrong, A. J. et al. Mol Cancer Res 9, 997-1007, doi:10.1158/1541-7786.MCR-10-0490 (2011).
36 Pantel, K. et al. Clin Chem 58, 936-940, doi:10.1373/clinchem.2011.175570 (2012).

Throughout this application various publications are referenced. The disclosures of these publications in their entireties are hereby incorporated by reference into this application in order to describe more fully the state of the art to which this invention pertains. Also incorporated herein by reference is the entire contents of U.S. provisional patent application No. 62/553,742, filed Sep. 1, 2017.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of detecting hepatocellular carcinoma recurrence or metastasis, the method comprising:
   (a) isolating hepatocyte circulating tumor cells (CTCs) from a blood sample obtained from a subject by contacting the CTCs with a set of capture antibodies, wherein the capture antibodies specifically bind asialoglycoprotein receptor (ASGPR), Glypican-3, and epithelial cell adhesion molecule (EpCAM) on the hepatocyte CTCs, thereby selectively isolating hepatocyte CTCs that express ASGPR, Glypican-3, and/or EpCAM from the blood sample;
   (b) contacting the isolated hepatocyte CTCs with an antibody that specifically binds vimentin;
   (c) measuring the number of vimentin-positive hepatocyte CTCs per 4 ml blood of the sample, wherein hepatocellular carcinoma recurrence or metastasis is detected when 2 or more vimentin-positive hepatocyte CTCs per 4 ml blood are present in the sample; and
   (d) treating the subject for advanced or metastatic hepatocellular carcinoma when 2 or more vimentin-positive hepatocyte CTCs per 4 ml blood are present in the sample.

2. The method of claim 1, wherein the contacting of steps (a) and/or (b) are performed using a microarray or nanosurface to which the antibodies are bound.

3. The method of claim 1, wherein the contacting of step (a) is performed with all of the capture antibodies bound to a single surface.

4. The method of claim 3, wherein the capture antibodies are bound to the surface via biotin-streptavidin binding.

5. The method of claim 1, wherein the contacting of step (a) is performed separately with each of the capture antibodies.

6. The method of claim 1, wherein the vimentin-positive cells are cytokeratin-positive and CD45-negative.

7. A method of measuring markers of hepatocellular carcinoma recurrence or metastasis in a blood sample obtained from a subject, the method comprising:
   (a) isolating hepatocyte circulating tumor cells (CTCs) by contacting the blood sample with a set of capture antibodies, wherein the capture antibodies specifically bind asialoglycoprotein receptor (ASGPR), Glypican-3, and epithelial cell adhesion molecule (EpCAM) on the hepatocyte CTCs, thereby selectively isolating hepatocyte CTCs that express ASGPR, Glypican-3, and/or EpCAM from the blood sample;
   (b) contacting the isolated hepatocyte CTCs with an antibody that specifically binds vimentin;
   (c) assigning a status score that reflects the measured amount of vimentin-positive isolated hepatocyte CTCs per volume of blood sample; and,
   (d) referring and treating the subject for surgical transplant when the status score is less than 2 vimentin-positive hepatocyte CTCs per 4 ml blood, or treating the subject for hepatocellular carcinoma when the status score is greater than or equal to 2 vimentin-positive hepatocyte CTCs per 4 ml blood.

8. A method of screening for advanced or metastatic hepatocellular carcinoma in a subject, the method comprising performing the method of claim 7; whereby advanced or metastatic hepatocellular carcinoma is detected when 2 or more vimentin-positive hepatocyte CTCs per 4 ml blood are present in the sample.

9. A method of identifying patients eligible for liver transplant, the method comprising performing the method of claim 7; whereby eligibility for liver transplant is detected when less than 2 vimentin-positive hepatocyte CTCs per 4 ml blood are present in the sample.

10. A method of treating cirrhosis in a subject, the method comprising:
  (a) isolating hepatocyte circulating tumor cells (CTCs) by contacting a blood sample obtained from the subject with a set of capture antibodies, wherein the capture antibodies specifically bind asialoglycoprotein receptor (ASGPR), Glypican-3, and epithelial cell adhesion molecule (EpCAM) on the hepatocyte CTCs, thereby selectively isolating hepatocyte CTCs that express ASGPR, Glypican-3, and/or EpCAM from the blood sample;
  (b) contacting the isolated hepatocyte CTCs with an antibody that specifically binds vimentin;
  (c) measuring the amount of vimentin-positive isolated hepatocyte CTCs per volume of blood sample;
  (d) assigning a status score that reflects the measured amount of vimentin-positive isolated hepatocyte CTCs per volume of blood sample; and
  (e) treating the subject with liver transplant when the status score is less than 2 vimentin-positive hepatocyte CTCs per 4 ml blood, or treating the subject for hepatocellular carcinoma when the status score is greater than or equal to 2 vimentin-positive hepatocyte CTCs per 4 ml blood.

11. A kit for detecting hepatocellular carcinoma recurrence or metastasis, the kit comprising:
  (a) a set of capture antibodies, wherein the capture antibodies specifically bind to asialoglycoprotein receptor (ASGPR), Glypican-3, and epithelial cell adhesion molecule (EpCAM) expressed on hepatocyte circulating tumor cells (CTCs); and
  (b) an antibody that specifically binds to vimentin on captured hepatocyte CTCs.

12. The kit of claim 11, further comprising:
  (c) a surface to which the set of capture antibodies are bound.

13. The kit of claim 11, wherein the capture antibodies are immobilized to a microarray or nanosurface.

14. The kit of claim 13, wherein the capture antibodies are bound to a single surface.

15. The kit of claim 13, wherein the capture antibodies are bound to the surface via biotin-streptavidin binding.

* * * * *